US011116414B2

(12) United States Patent
Sawado et al.

(10) Patent No.: US 11,116,414 B2
(45) Date of Patent: Sep. 14, 2021

(54) BIOLOGICAL ANALYSIS DEVICE, BIOLOGICAL ANALYSIS METHOD, AND PROGRAM

(71) Applicant: SEIKO EPSON CORPORATION, Tokyo (JP)

(72) Inventors: Ayae Sawado, Kai (JP); Kohei Yamada, Shiojiri (JP); Akiko Yamada, Shiojiri (JP); Megumi Enari, Shiojiri (JP); Yuta Machida, Chino (JP); Akira Ikeda, Chino (JP); Masayasu Fukuoka, Shiojiri (JP); Akira Kitahara, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 303 days.

(21) Appl. No.: 15/998,546

(22) Filed: Aug. 16, 2018

(65) Prior Publication Data
US 2019/0053720 A1 Feb. 21, 2019

(30) Foreign Application Priority Data

Aug. 16, 2017 (JP) .............................. JP2017-157160
May 31, 2018 (JP) .............................. JP2018-104932

(51) Int. Cl.
*A61B 5/026* (2006.01)
*A61B 5/021* (2006.01)
(Continued)

(52) U.S. Cl.
CPC ........ *A61B 5/0261* (2013.01); *A61B 5/02116* (2013.01); *A61B 5/02438* (2013.01);
(Continued)

(58) Field of Classification Search
CPC ... A61B 5/0261; A61B 5/7275; A61B 5/1072; A61B 5/7242; A61B 5/02116;
(Continued)

(56) References Cited

U.S. PATENT DOCUMENTS

| 5,913,826 A | 6/1999 | Blank |
| 2002/0002339 A1 | 1/2002 | Sugo et al. |

(Continued)

FOREIGN PATENT DOCUMENTS

| JP | 2001-321347 A | 11/2001 |
| JP | 2004-154231 A | 6/2004 |

(Continued)

OTHER PUBLICATIONS

Masaki Goma et al. "The Development of Small Laser Doppler Blood Flow Sensor". Pioneer R&D, vol. 21, No. 1, 2012, pp. 30-36.

(Continued)

*Primary Examiner* — Christopher Koharski
*Assistant Examiner* — Kaitlyn E Selmer
(74) *Attorney, Agent, or Firm* — Oliff PLC

(57) ABSTRACT

A biological analysis device includes a blood vessel calculation unit that calculates a blood vessel index related to a blood vessel of a biological body in accordance with a blood mass integration value obtained by integrating blood mass indexes relate to a blood mass of the biological body during an integration period and a blood flow integration value obtained by integrating blood flow indexes related to a blood flow of the biological body during the integration period.

11 Claims, 11 Drawing Sheets

(51) Int. Cl.
   *A61B 5/024* (2006.01)
   *A61B 5/00* (2006.01)
   *A61B 5/107* (2006.01)

(52) U.S. Cl.
   CPC ............ *A61B 5/1072* (2013.01); *A61B 5/681* (2013.01); *A61B 5/6824* (2013.01); *A61B 5/7242* (2013.01); *A61B 5/7275* (2013.01)

(58) Field of Classification Search
   CPC ... A61B 5/681; A61B 5/6824; A61B 5/02438; G16H 50/30
   See application file for complete search history.

(56) References Cited

U.S. PATENT DOCUMENTS

| | | | | |
|---|---|---|---|---|
| 2011/0319775 | A1* | 12/2011 | Fujii | A61B 3/1233 600/504 |
| 2015/0018693 | A1 | 1/2015 | Mestha et al. | |
| 2015/0216458 | A1* | 8/2015 | Kasahara | A61B 5/14532 600/316 |
| 2016/0174854 | A1* | 6/2016 | Nishida | A61B 5/02007 600/480 |
| 2019/0090818 | A1* | 3/2019 | Nakajima | A61B 5/746 |
| 2019/0380598 | A1 | 12/2019 | Higuchi | |
| 2020/0276380 | A1 | 9/2020 | Maierhofer et al. | |

FOREIGN PATENT DOCUMENTS

| | | |
|---|---|---|
| JP | 2008-018035 A | 1/2008 |
| JP | 2016-146958 A | 8/2016 |
| JP | 2016-150065 A | 8/2016 |
| WO | 2012/142455 A2 | 10/2012 |
| WO | 2015/199159 A1 | 12/2015 |
| WO | 2016/130083 A1 | 8/2016 |

OTHER PUBLICATIONS

U.S. Appl. No. 16/103,968, filed Aug. 16, 2018 in the name of Megumi Enari et al.
U.S. Appl. No. 15/998,545, filed Aug. 16, 2018 in the name of Kohei Yamada et al.
Sep. 1, 2020 Office Action issued U.S. Appl. No. 15/998,545.
Dec. 17, 2020 Office Action issued in U.S. Appl. No. 15/998,545.
Jan. 11, 2021 U.S. Office Action issued in U.S. Appl. No. 16/103,968.
Jun. 25, 2021 Office Action issued in U.S. Appl. No. 16/103,968.

* cited by examiner

BIOLOGICAL ANALYSIS DEVICE, BIOLOGICAL ANALYSIS METHOD, AND PROGRAM

BACKGROUND

1. Technical Field

The present invention relates to a technology for analyzing a biological body.

2. Related Art

Various measurement technologies for analyzing biological information such as a pulse wave velocity have been proposed in the related art. For example, JP-A-2008-18035 discloses a measurement device that measures a pulse wave velocity using cuffs mounted on an upper limb and a lower limb of a biological body. Specifically, a pulse wave velocity of a biological body is calculated using a temporal difference between a pulse wave detected with the cuff on the upper limb and a pulse wave detected with the cuff on the lower limb.

In the technology of JP-A-2008-18035, since it is necessary to mount the cuffs on the upper limb and the lower limb of the biological body, a burden on a subject (user) is large.

SUMMARY

A biological analysis device according to a preferred aspect of the invention includes a blood vessel calculation unit that calculates a blood vessel index related to a blood vessel of a biological body in accordance with a blood mass integration value obtained by integrating blood mass indexes relate to a blood mass of the biological body during an integration period and a blood flow integration value obtained by integrating blood flow indexes related to a blood flow of the biological body during the integration period.

A biological analysis method according to a preferred aspect of the invention includes calculating a blood vessel index related to a blood vessel of a biological body in accordance with a ratio of a blood mass integration value obtained by integrating blood mass indexes relate to a blood mass of the biological body during an integration period and a blood flow integration value obtained by integrating blood flow indexes related to a blood flow of the biological body during the integration period.

A program according to a preferred aspect of the invention causes a computer to function as a blood vessel calculation unit that calculates a blood vessel index related to a blood vessel of a biological body in accordance with a ratio of a blood mass integration value obtained by integrating blood mass indexes relate to a blood mass of the biological body during an integration period and a blood flow integration value obtained by integrating blood flow indexes related to a blood flow of the biological body during the integration period.

BRIEF DESCRIPTION OF THE DRAWINGS

The invention will be described with reference to the accompanying drawings, wherein like numbers reference like elements.

FIG. 3 is a diagram illustrating a configuration in which a function of the biological analysis device is focused on.

DESCRIPTION OF EXEMPLARY EMBODIMENTS

First Embodiment

Figure 1:
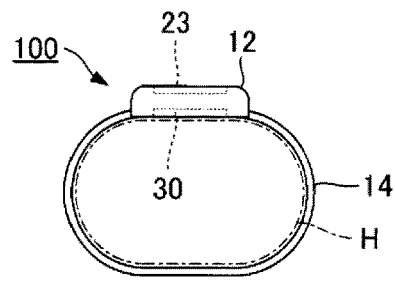
FIG. 1 is a side view illustrating a biological analysis device according to a first embodiment of the invention.
Figure 2:
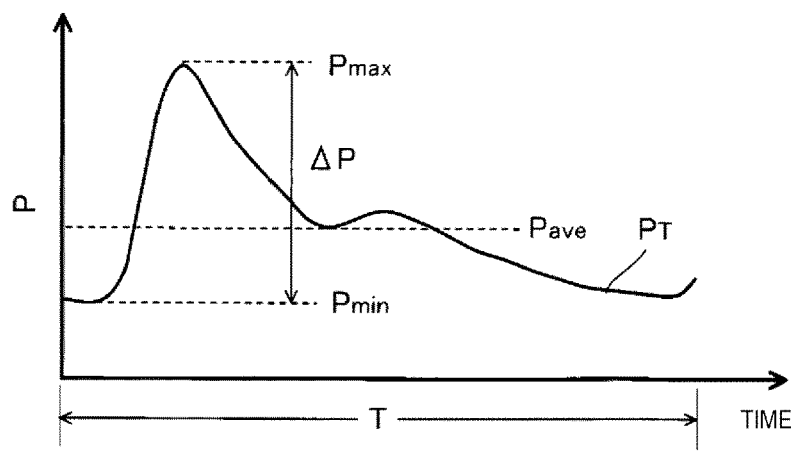
FIG. 2 is a graph illustrating a temporal change in a blood pressure.

FIG. 1 is a side view illustrating a biological analysis device 100 according to a first embodiment of the invention. The biological analysis device 100 is a measurement instrument that measures biological information of a subject (user) in a non-invasive manner. The biological analysis device 100 according to the first embodiment measures a pulse pressure ΔP of a specific part (hereinafter referred to as a "measurement region") H of the body of a subject as biological information. In the following description, a wrist or an upper arm of the subject is exemplified as the measurement region H. FIG. 2 is a graph illustrating a temporal change PT in a blood pressure P. A difference between a systolic blood pressure (maximum pressure) Pmax and a diastolic blood pressure (minimum pressure) Pmin is the pulse pressure ΔP. In the first embodiment, a change mass of the blood pressure P during an analysis period (about 0.5 to 1 second) T equivalent to one beat is assumed to be the pulse pressure ΔP. A time length of the analysis period T is not limited to one beat. For example, a period longer than a time length equivalent to one beat may be set as the analysis period T. Pave in FIG. 2 is an average blood pressure during the analysis period T.

Expression (1) shows a pressure caused by water hammer phenomenon, and the blood pressure P is equal to the pressure of water hammer phenomenon. As understood from Expression (1), the blood pressure P is expressed as a product of blood density ρ, a pulse wave velocity PWV, and a blood flow rate V of a blood vessel.

$$P = \rho \times PWV \times \quad (1)$$

Since a temporal change in the blood density ρ and the pulse wave velocity PWV is small, an amount of change of the blood density ρ and an amount of change of the pulse wave velocity PWV during the analysis period T can be considered to be constant. Accordingly, as expressed in Expression (2), the pulse pressure (that is, an amount of change of a pressure during the analysis period T) ΔP is expressed as a product of the blood density ρ, the pulse wave velocity PWV, and an amount of change (that is, an amplitude of a temporal change in the blood flow rate of a biological body) ΔV of the blood flow rate V during the analysis period T. The blood density ρ can be set to a predetermined value (for example, 1070 kg/m$^3$) since an individual difference is small. That is, by calculating the pulse wave velocity PWV and an amplitude (hereinafter referred to as a "blood flow rate amplitude") ΔV of the blood flow rate V, it is possible to calculate the pulse pressure ΔP.

$$\Delta P = \rho \times PWV \times \Delta V \quad (2)$$

The biological analysis device 100 in FIG. 1 is mounted on the measurement region H (an upper arm or a wrist). The biological analysis device 100 according to the first embodiment is a wrist watch type portable device including a casing 12 and a belt 14. The biological analysis device 100 is mounted on the body of the subject by winding the belt 14 around the measurement region H.

Figure 3:
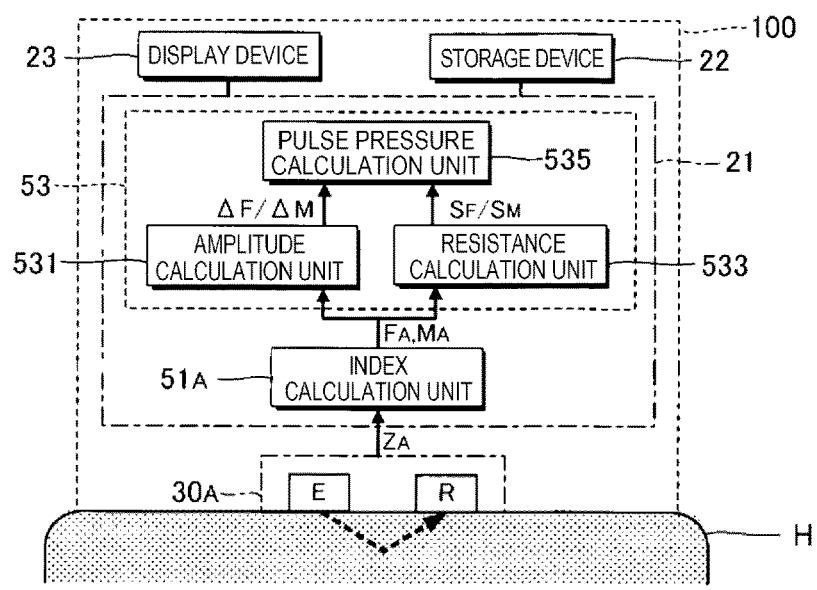

FIG. 3 is a diagram illustrating a configuration in which a function of the biological analysis device 100 is focused on. The biological analysis device 100 according to the first embodiment includes a control device 21, a storage device 22, a display device 23, and a detection device 30A. The control device 21 and the storage device 22 are installed inside the casing 12.

The display device 23 (for example, a liquid crystal panel) is installed on, for example, a surface of the casing 12 opposite to the measurement region H, as illustrated in FIG. 1. The display device 23 displays various images including a measurement result under the control of the control device 21.

The detection device 30A in FIG. 3 is an optical sensor module that generates a detection signal ZA in accordance with a state of the measurement region H. Specifically, the detection device 30A includes a light-emitting unit E and a light-receiving unit R. The light-emitting unit E and the light-receiving unit R are installed at, for example, positions (generally, a surface in contact with the measurement region H) of the casing 12 opposite to the measurement region H.

The light-emitting unit E is a light source that radiates light to the measurement region H. The light-emitting unit E according to the first embodiment radiates a coherent laser beam to the measurement region H (biological body) with a narrowband. For example, a light-emitting element such as a vertical cavity surface emitting LASER (VCSEL) that emits a laser beam by resonance in a resonator is used appropriately as the light-emitting unit E. The light-emitting unit E according to the first embodiment radiates, for example, light with a predetermined wavelength (for example, 800 nm to 1300 nm) in a near infrared area to the measurement region H. The light-emitting unit E emits light under the control of the control device 21. The light emitted by the light-emitting unit E is not limited to the near infrared light.

Light incident on the measurement region H from the light-emitting unit E is repeatedly diffused and reflected while passing through the inside of the measurement region H to exit to the side of the casing 12. Specifically, the light passing through blood vessels inside the measurement region H and blood in the blood vessels such as an artery (for example, a brachial artery, a radial artery, or an ulnar artery) exits from the measurement region H to the side of the casing 12.

The light-receiving unit R receives the laser beam reflected from the inside of the measurement region H. Specifically, the light-receiving unit R generates a detection signal ZA indicating a light reception level of the light passing through the measurement region H. For example, a light-receiving element such as a photodiode (PD) that generates charges in accordance with the light reception intensity is used as the light-receiving unit R. Specifically, a light-receiving element in which a photoelectric conversion layer is formed of indium, gallium, and arsenic (InGaAs) having high sensitivity in a near infrared area is suitable as the light-receiving unit R. As understood from the above description, the detection device 30A according to the first embodiment is a reflective optical sensor in which the light-emitting unit E and the light-receiving unit R are located on side of the measurement region H. Here, a transmissive optical sensor in which the light-emitting unit E and the light-receiving unit R are located on opposite sides with the measurement region H interposed therebetween may be used as the detection device 30A. The detection device 30A includes, for example, a driving circuit that drives the light-emitting unit E by applying a driving current and output circuits (for example, an amplification circuit and an A/D converter) that perform amplification and A/D conversion on a signal output by the light-receiving unit R, but these circuits are not illustrated in FIG. 3.

The light arriving at the light-receiving unit R includes a component diffused and reflected from a tissue (a stationary tissue) stationary inside the measurement region H and a component diffused and reflected from an object (generally, a red blood cell) moving inside a blood vessel inside the measurement region H. The frequency of light before and after the diffusion and reflection from a stationary tissue is not changed. However, before and after diffusion and reflection from a red blood cell, the frequency of light is changed by an amount of change (hereinafter referred to as a "frequency shift amount" proportional to a movement speed (that is, a blood flow rate) of the red blood cell. That is, the light passing through the measurement region H and arriving at the light-receiving unit R contains a component that is changed (frequency-shifted) by the frequency shift amount with respect to the frequency of the light emitting the light-emitting unit E. The detection signal ZA supplied to the control device 21 is an optical beat signal in which the frequency shift by a blood flow inside the measurement region H is reflected.

The control device 21 in FIG. 3 is an arithmetic processing device such as a central processing unit (CPU) or a field-programmable gate array (FPGA) and controls the whole biological analysis device 100. The storage device 22 includes, for example, a nonvolatile semiconductor memory and stores a program to be executed by the control device 21 and various kinds of data to be used by the control device 21. A configuration in which functions of the control device 21 are distributed to a plurality of integrated circuits can be adopted or a configuration in which some or all of the functions of the control device 21 are realized by a dedicated electronic circuit can also be adopted. In FIG. 3, the control device 21 and the storage device 22 are illustrated as separate elements, but the control device 21 containing the storage device 22 can also be realized by, for example, an application specific integrated circuit (ASIC) or the like.

The control device 21 according to the first embodiment realizes a plurality of functions (an index calculation unit 51A and a blood vessel calculation unit 53) of calculating the pulse pressure ΔP from the detection signal ZA generated by the detection device 30A by executing a program stored in the storage device 22. Some of the functions of the control device 21 may be realized by a dedicated electronic circuit.

The index calculation unit 51A in FIG. 3 calculates a blood mass index MA and a blood flow index FA of the measurement region H from the detection signal ZA generated by the detection device 30A. The blood mass index MA (so-called MASS value) is an index related to a blood mass (specifically, the number of red blood cells in a unit volume) of a biological body. A blood mass is changed in conjunction with pulsation of a blood vessel diameter synchronized with a beat of a heart. That is, the blood mass index MA also correlates with a blood vessel diameter. Accordingly, the blood mass index MA can be paraphrased as an index of a blood vessel diameter (further, a unit area of a blood vessel) of a biological body. On the other hand, the blood flow index FA (so-called FLOW value) is an index related to a blood flow of a biological body (that is, a volume of blood moving in an artery in a unit time).

The index calculation unit 51A calculates an intensity spectrum from the detection signal ZA and calculates the blood mass index MA and the blood flow index FA from the intensity spectrum. The intensity spectrum is a distribution of an intensity (power or amplitude) G(f) of a signal component of the detection signal ZA at each frequency (Doppler frequency) on a frequency axis. In the calculation of the intensity spectrum, any known frequency analysis such as fast Fourier transform (FFT) can be adopted. The calculation of the intensity spectrum is executed repeatedly at a period shorter than the analysis period T.

The blood mass index MA is expressed in Expression (3a) below. A sign $\langle I^2 \rangle$ in Expression (3a) is an average intensity over the whole bandwidth of the detection signal ZA or an intensity G(0) (that is, an intensity of a direct-current component) at 0 Hz in the intensity spectrum.

$$M = \frac{\int_{f_L}^{f_H} G(f) df}{\langle I^2 \rangle} \tag{3a}$$

Figure 4:
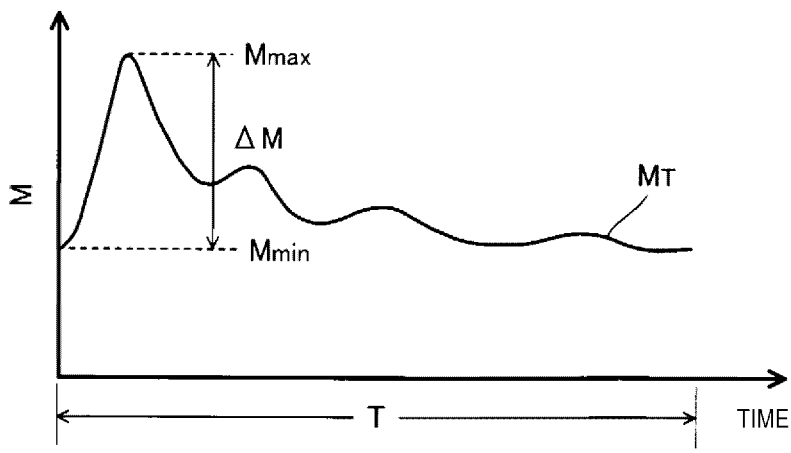
FIG. 4 is a graph illustrating a temporal change in a blood mass index.

As understood from Expression (3a), the blood mass index MA is calculated by integrating the intensity G(f) of each frequency f in the intensity spectrum in a range between a lower limit fL and upper limit fH on the frequency axis. The lower limit fL is less than the upper value fH. The blood mass index MA may be calculated by calculating Expression (3b) below in which an integral of Expression (3a) is replaced with a total sum (Σ). The sign Δf in Expression (3b) is a bandwidth corresponding to one intensity G(f) on the frequency axis and is equivalent to a horizontal width of each rectangle when the intensity spectrum is approximated with a plurality of rectangles arranged on the frequency axis. The calculation of the blood mass index MA is repeatedly executed at a period shorter than the analysis period T. FIG. 4 illustrates a temporal change MT in the blood mass index M (MA) calculated during the analysis unit T by the index calculation unit 51A. In addition to the blood mass index MA according to the first embodiment, blood mass indexes MC to be exemplified in each embodiment to be described below are also calculated as the blood mass index M of Expression (3a) or (3b). As understood from the above description, the blood mass index M is calculated (specifically, the intensity of each frequency in the intensity spectrum is integrated in a predetermined frequency range) from an intensity spectrum related to the frequency of light reflected and received inside in a biological body by radiating a laser beam.

$$M = \frac{\sum_{f=f_L}^{f_H} \Delta f \cdot G(f)}{\langle I^2 \rangle} \tag{3b}$$

The blood mass index FA is expressed in Expression (4a) below.

$$F = \frac{\int_{f_L}^{f_H} f \cdot G(f) df}{\langle I^2 \rangle} \tag{4a}$$

Figure 5:
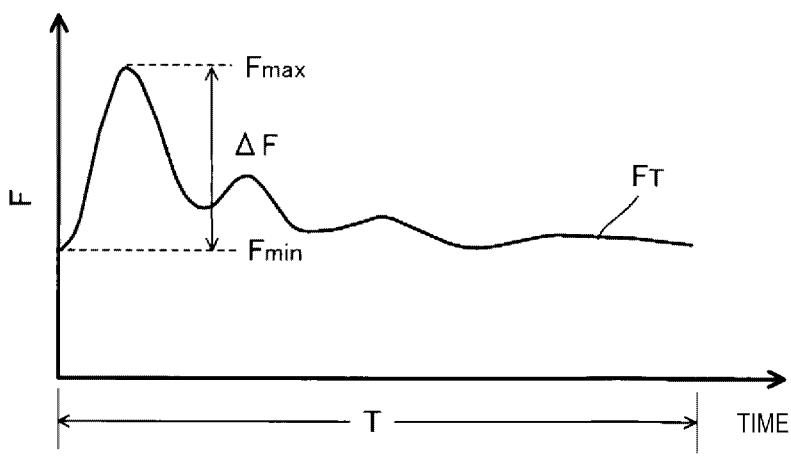
FIG. 5 is a graph illustrating a temporal change in a blood flow index.

As understood from Expression (4a), the blood flow index FA is calculated by integrating a product (f× G(f)) of the intensity G(f) of each frequency f in the intensity spectrum and the frequency f in a range between a lower limit fL and an upper limit fH on the frequency axis. Hereinafter, the product (f×G(f)) of the intensity G(f) of each frequency f in the intensity spectrum and the frequency f is referred to as a "frequency weighted intensity spectrum". The blood mass index FA may be calculated by calculating Expression (4b) below in which an integral of Expression (4a) is replaced with a total sum (Σ). The blood mass index FA is repeatedly calculated at a period shorter than the analysis period T. FIG. 5 illustrates a temporal change FT in the blood flow index F (FA) calculated during the analysis unit T by the index calculation unit 51A. In addition to the blood flow index FA according to the first embodiment, blood flow indexes FB to be exemplified in each embodiment to be described below are also calculated as the blood flow index F of Expression (4a) or (4b). As understood from the above description, the blood flow index F is calculated (specifically, the product of the intensity of each frequency in the intensity spectrum and the frequency is integrated in a predetermined frequency range) from an intensity spectrum related to the frequency of light reflected and received inside in a biological body by radiating a laser beam.

$$F = \frac{\sum_{f=f_L}^{f_H} f \cdot \Delta f \cdot G(f)}{\langle I^2 \rangle} \quad (4b)$$

The blood vessel calculation unit 53 in FIG. 3 calculates the pulse pressure ΔP of the measurement region H using the blood mass index MA and the blood flow index FA calculated by the index calculation unit 51A. The blood vessel calculation unit 53 according to the first embodiment includes an amplitude calculation unit 531, a resistance calculation unit 533, and a pulse pressure calculation unit 535.

The amplitude calculation unit 531 calculates an index related to the blood flow amplitude ΔV (hereinafter referred to as an "amplitude index") using the blood mass index MA and the blood flow index FA generated by the index calculation unit 51A. Specifically, the amplitude calculation unit 531 calculates an amplitude index in accordance with an amplitude ΔM of the temporal change MT in the blood mass index MA and an amplitude ΔF of the temporal change FT in the blood mass index F. As exemplified in FIG. 4, the amplitude ΔM is a difference between the maximum value Mmax and the minimum value Mmin of the blood mass index MA during the analysis period T. As exemplified in FIG. 5, the amplitude ΔF is a difference between the maximum value Fmax and the minimum value Fmin the blood flow index FA during the analysis period T.

Figure 6:
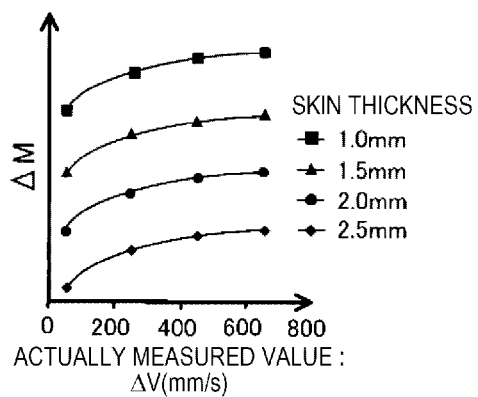
FIG. 6 is a graph illustrating a relation between a blood flow rate amplitude actually measured on a subject and an amplitude of a temporal change in a calculated blood mass index in a plurality of cases in which a skin thickness of the subject is changed.
Figure 7:
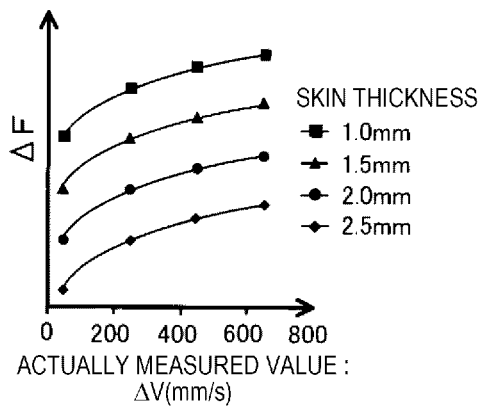
FIG. 7 is a graph illustrating a relation between a blood flow rate amplitude actually measured on a subject and an amplitude of a temporal change in a calculated blood flow index in a plurality of cases in which a skin thickness of the subject is changed.
Figure 8:
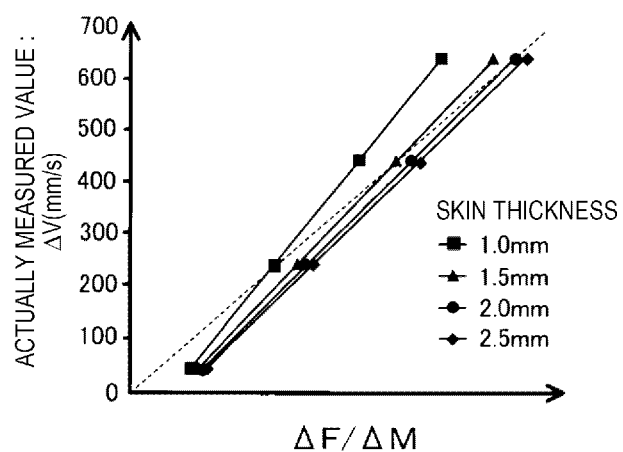
FIG. 8 is a graph illustrating a relation between a blood flow rate amplitude actually measured on a subject and a ratio of an amplitude of a temporal change in a blood mass index and an amplitude of a temporal change in the blood flow index in a plurality of cases in which a skin thickness of the subject is changed.

FIG. 6 is a graph illustrating a relation between the blood flow rate amplitude ΔV actually measured on the subject and the amplitude ΔM specified by the index calculation unit 51A. FIG. 7 is a graph illustrating a relation between the blood flow rate amplitude ΔV actually measured on the subject and the amplitude ΔF specified by the index calculation unit 51A. FIGS. 6 and 7 illustrate a plurality of cases in which a skin thickness of the subject is changed. The skin thickness is a distance between the surface of the skin and a blood vessel. The blood flow rate amplitude ΔV is an actually measured value by a known measurement technology. As ascertained from FIGS. 6 and 7, each of the amplitude ΔM and the amplitude ΔF correlates with the blood flow amplitude ΔV and is considerably changed in accordance with a skin thickness. FIG. 8 is a graph illustrating a relation between the blood flow rate amplitude ΔV actually measured on the subject and a ratio of the amplitude ΔM and the amplitude ΔF specified by the index calculation unit 51A (specifically, a ratio of the amplitude ΔF to the amplitude ΔM) in the plurality of cases in which the skin thickness of the subject is changed. As ascertained from FIG. 8, it is possible to obtain the knowledge that the ratio (ΔF/ΔM) of the amplitude ΔF to the amplitude ΔM positively correlates with the blood flow rate amplitude ΔV (when one of the amplitudes increases, the other also increases) and a change in accordance with the skin thickness is small. As a background of the foregoing knowledge, the amplitude calculation unit 531 according to the first embodiment calculates the ratio (ΔF/ΔM) of the amplitude ΔF to the amplitude ΔM as an amplitude index.

The resistance calculation unit 533 in FIG. 3 calculates an index related to the pulse wave velocity PWV using the blood mass index MA and the blood flow index FA generated by the index calculation unit 51A. The pulse wave velocity PWV correlates with blood vessel resistance. Specifically, when the blood vessel resistance is high, the pulse wave velocity PWV tends to be faster. On the basis of this tendency, an index related to the pulse wave velocity PWV is referred to as a "resistance index". That is, the resistance calculation unit 533 calculates a resistance index using the blood mass index MA and the blood flow index FA. Specifically, the resistance index is calculated in accordance with a value (hereinafter referred to as a "blood mass integration value") SM obtained by integrating the blood mass index MA during an integration period and a value (hereinafter referred to as a "blood mass integration value") SF obtained by integrating the blood flow index FA during the integration period. For example, the integration period is identical to the analysis period T (that is, a period equivalent to one of beats). The integration period may be different from the analysis period T.

In the first embodiment, the resistance index is calculated in accordance with the blood mass integration value SM obtained by integrating a normalized blood mass index MN during the analysis period T and the blood flow integration value SF obtained by integrating the normalized blood flow index FN during the analysis period T. The normalized blood mass index MN is a numerical value obtained by normalizing the blood mass index MA within a normalization range, and the normalized blood flow index FN is a numerical value obtained by normalizing the blood flow index FA within the normalization range.

Figure 9:
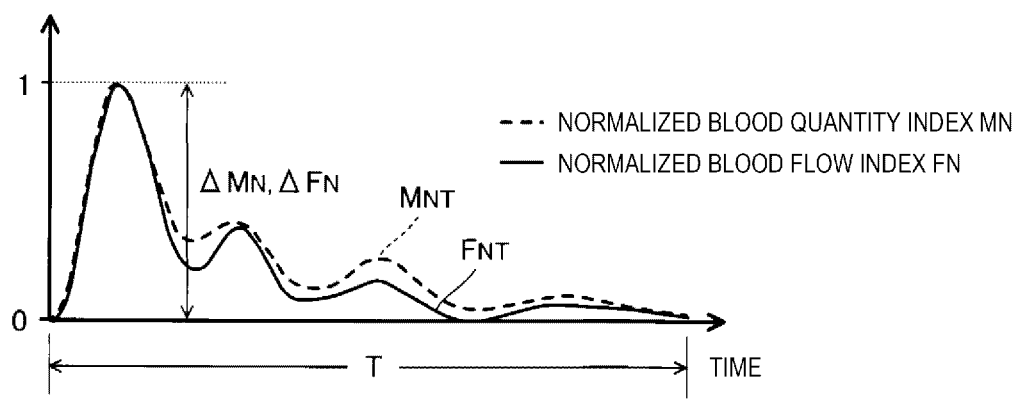
FIG. 9 is a graph illustrating a temporal change in a normalized blood quality index and a temporal change in a normalized blood flow index.

FIG. 9 is a graph illustrating a temporal change MNT in a normalized blood quality index MN and a temporal change FNT in a normalized blood flow index FN. FIG. 9 illustrates a case in which each of the blood mass index (blood quantity index) MA and the blood flow index FA is normalized in a normalization range equal to or greater than 0 and equal to or less than 1. That is, the blood mass index MA and the blood flow index FA are normalized so that the minimum value Mmin and the minimum value Fmin during the analysis period T are 0 and the maximum value Mmax and the maximum value Fmax during the analysis period T are 1. That is, the amplitude DMN of the normalized blood mass index MN and the amplitude DFN of the normalized blood flow index FN are 1. Specifically, the blood mass integration value SM is a temporal integration value of the normalized blood mass index MN during the analysis period T, and the blood flow integration value SF is a temporal integration value of the normalized blood flow index FN during the analysis period T. The area of a region surrounded by a curve line representing a temporal change MNT of the normalized blood mass index MN and a time axis (a straight line of MN=0) is the blood mass integration value SM, and the area of a region surrounded by a curve line representing a temporal change FNT of the normalized blood flow index FN and a time axis (a straight line of FN=0) is the blood flow integration value SF.

Figure 10:
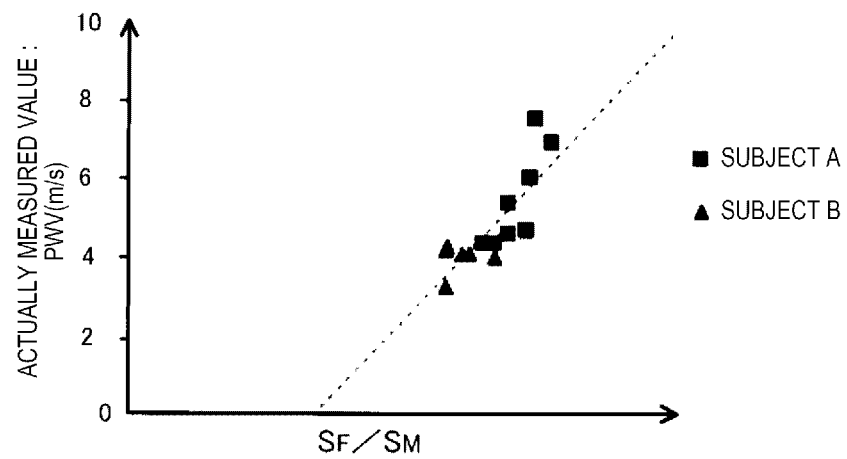
FIG. 10 is a graph illustrating a relation between a pulse wave velocity actually measured on a plurality of subjects and a ratio of a blood mass integration value and a blood flow integration value in the subjects.

FIG. 10 is a graph illustrating a relation between the pulse wave velocity PWV actually measured on a plurality of subjects and a ratio of the blood mass integration value SM and the blood flow integration value SF on subjects. The pulse wave velocity PWV is an actually measured value by a known measurement technology. As ascertained from FIG. 10, it is possible to obtain the knowledge that the pulse wave velocity PWV correlates with the ratio of the blood mass integration value SM and the blood mass integration value SF (specifically, a ratio of the blood flow integration value SF to the blood mass integration value SM). As a background of the foregoing knowledge, the resistance calculation unit 533 according to the first embodiment calculates the ratio (SF/SM) of the blood mass integration value SM and the blood flow integration value SF as a resistance index.

Figure 11:
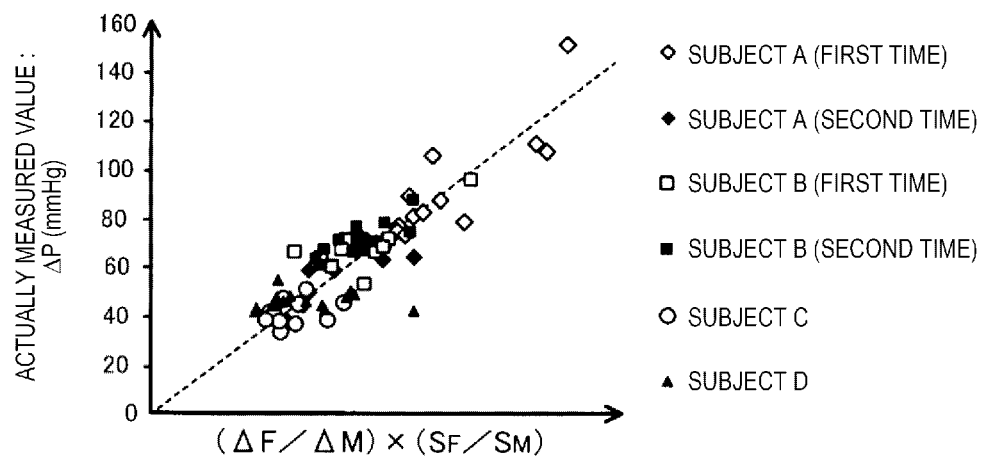
FIG. 11 is a graph illustrating a relation between a pulse pressure actually measured on a subject and a plurality of product of an amplitude index and a resistance index on the subjects.

The pulse pressure calculation unit 535 in FIG. 3 calculates the pulse pressure ΔP in accordance with the amplitude index calculated by the amplitude calculation unit 531 and the resistance index calculated by the resistance calculation unit 533. Specifically, the pulse pressure calculation unit 535 calculates the pulse pressure ΔP in accordance with the product of the amplitude index and the resistance index using Expression (2) described above. FIG. 11 is a graph illustrating a relation between the pulse pressure ΔP actually measured on a plurality of subject and a product ((ΔF/ΔM)×(SF/SM)) of the amplitude index and a resistance index on the subjects. The pulse pressure ΔP is an actually measured value by a known measurement technology. As ascertained from FIG. 11, the product of the amplitude index and the resistance index correlates with (specifically, has a proportional relation with) the pulse pressure ΔP. Accordingly, the pulse pressure ΔP is expressed in Expression (5a) below. As understood from Expression (5a), the pulse pressure ΔP can be calculated by multiplying the product of the amplitude index and the resistance index (SF/SM) by a predetermined coefficient K. For example, the coefficient K is set in accordance with an attribute (for example, age, sex, and weight) of the subject. As understood from the above-description, the blood vessel calculation unit 53 functions as an element that calculates the pulse pressure ΔP in accordance with the blood mass integration value SM and the blood flow integration value SF. The control device 21 causes the display device 23 to display the pulse pressure ΔP calculated by the blood vessel calculation unit 53.

$$\Delta P = K \times \frac{SF}{SM} \times \frac{\Delta F}{\Delta M} \quad (5a)$$

Figure 12:
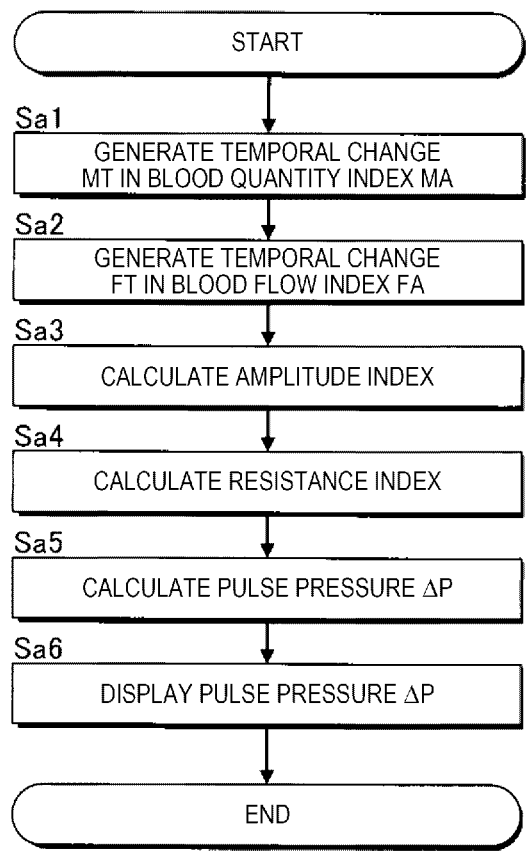
FIG. 12 is a flowchart illustrating a biological analysis process executed by a control device.

FIG. 12 is a flowchart illustrating a process (hereinafter referred to as a "biological analysis process") executed by the control device 21. The biological analysis process in FIG. 12 is executed during each analysis period T on the time axis. When the biological analysis process starts, the index calculation unit 51A generates the temporal change MT in the blood mass index (blood quantity index) MA during the analysis period T (Sa1). In the calculation of the blood mass index MA, Expression (3a) or (3b) described above is used. Subsequently, the index calculation unit 51A generates the temporal change FT in the blood flow index FA during the analysis period T (Sa2). In the calculation of the blood flow index FA, Expression (4a) or (4b) described above is used.

The amplitude calculation unit 531 calculates the amplitude index in accordance with the amplitude ΔM of the temporal change MT and the amplitude ΔF of the temporal change FT generated by the index calculation unit 51A (Sa3). Specifically, the ratio (ΔF/ΔM) of the amplitude ΔM and the amplitude ΔF is calculated as the amplitude index. Subsequently, the resistance calculation unit 533 calculates the resistance index from the temporal change MT and the temporal change FT generated by the index calculation unit 51A (Sa4). Specifically, the ratio (SF/SM) of the blood mass integration value SM and the blood flow integration value SF is calculated as the resistance index. The pulse pressure calculation unit 535 calculates the pulse pressure ΔP in accordance with the amplitude index calculated by the amplitude calculation unit 531 and the resistance index calculated by the resistance calculation unit 533 (Sa5). The processes from step Sa3 to step Say is a process of calculating the pulse pressure ΔP in accordance with the blood mass integration value SM and the blood flow integration value SF. Specifically, the pulse pressure ΔP in accordance with a product of the amplitude index and the resistance index is calculated. The control device 21 causes the display device 23 to display the pulse pressure ΔP calculated by the pulse pressure calculation unit 535 (Sa6). The order of the generation (Sa1) of the temporal change MT in the blood mass index MA and the generation (Sa2) of the temporal change FT in the blood flow index FA may be reversed. By executing the above-described biological analysis process during each analysis period T, a time series (that is, a temporal change in the pulse pressure ΔP) of the plurality of pulse pressures ΔP is calculated. The order of the process (Sa3) of calculating the amplitude index and the process (Sa4) of calculating the resistance index may be reversed.

Figure 13:
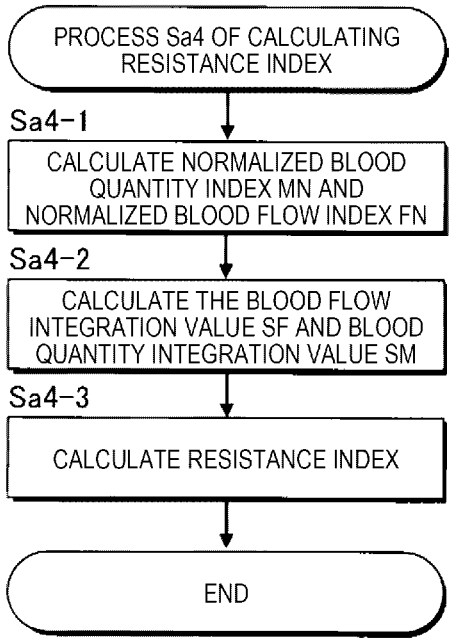
FIG. 13 is a flowchart illustrating specific content of a process of calculating a resistance index.

FIG. 13 is a flowchart illustrating specific content of a process Sa4 of calculating the resistance index. The resistance calculation unit 533 calculates the normalized blood mass index (normalized blood quantity index) MN and the normalized blood flow index FN respectively obtained by normalizing the blood mass index (blood quantity index) MA and the blood flow index FA within a normalization range (Sa4-1). Subsequently, the resistance calculation unit 533 calculates the blood mass integration value SM and the blood flow integration value SF respectively obtained by integrating the normalized blood mass index MN and the normalized blood flow index FN during the analysis period T (Sa4-2). The resistance calculation unit 533 calculates the ratio (SF/SM) of the blood mass integration value SM and the blood flow integration value SF as the resistance index (Sa4-3).

As described above, in the first embodiment, the amplitude index (ΔF/ΔM) is calculated in accordance with the amplitude ΔM of the temporal change MT in the blood mass index MA and the amplitude ΔF of the temporal change FT in the blood flow index FA, the resistance index (SF/SM) is calculated in accordance with the blood mass integration value SM and the blood flow integration value SF, and the pulse pressure ΔP is calculated from the amplitude index and the resistance index. In each calculation of the foregoing indexes (the amplitude index, the resistance index, and the pulse pressure ΔP), a cuff is unnecessary in principle.

Accordingly, it is possible to calculate the pulse pressure ΔP with high precision while reducing a physical load of a subject.

In the first embodiment, in particular, it is possible to calculate the pulse pressure ΔP with high precision using the tendency of the correlation of the product of the ratio (ΔF/ΔM) of the amplitude ΔM and the amplitude ΔF and the ratio (SF/SM) of the blood mass integration value SM and the blood flow integration value SF with the pulse pressure ΔP. Further, by taking the ratio of the amplitude ΔM of the blood mass index MA and the amplitude ΔF of the blood flow index FA, it is possible to calculate an amplitude index with high precision even when a skin thickness is changed.

Second Embodiment

A second embodiment of the invention will be described. Elements similar to those of the first embodiment in operations or functions in each embodiment to be exemplified below, the reference numerals used in the description of the first embodiment are applied, and a detailed description of each element will be appropriately omitted.

Figure 14:
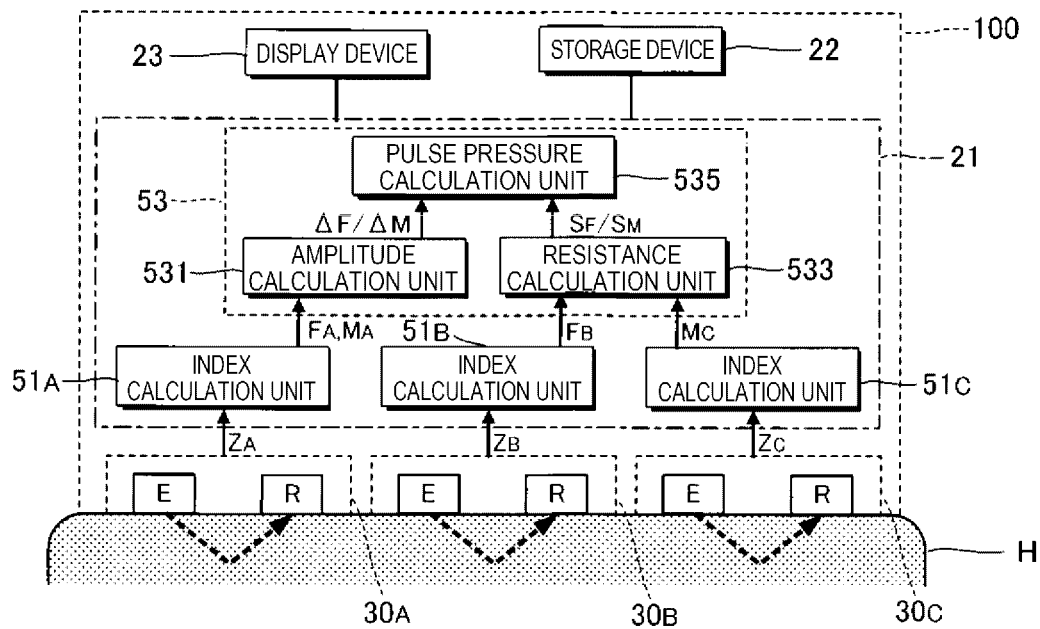
FIG. 14 is a diagram illustrating a configuration of a biological analysis device according to a second embodiment.

FIG. 14 is a diagram illustrating a configuration in which a biological analysis device 100 is focused on according to the second embodiment. A biological analysis device 100 according to the second embodiment has a configuration in which a detection device 30B, a detection device 30C, an index calculation unit 51B, and an index calculation unit 51C are added to the biological analysis device 100 of the first embodiment. In the first embodiment, the amplitude index and the resistance index have been calculated using the detection signal ZA generated by the detection device 30A. In the second embodiment, however, the amplitude index is calculated using the detection signal ZA generated by the detection device 30A and the resistance index is calculated using detection signals Z (ZB and ZC) generated by two separate detection devices 30 (30B and 30C) separate from the detection device 30A, respectively.

The detection device 30A according to the second embodiment has a configuration and a function similar to those of the first embodiment and generates a detection signal ZA in accordance with a state of the measurement region H. The detection device 30B includes a light-emitting unit R and a light-receiving unit E similar to those of the detection device 30A and generates a detection signal ZB in accordance with a state of the measurement region H. Similarly, the detection device 30C includes a light-emitting unit R and a light-receiving unit E and generates a detection signal ZC in accordance with a state of the measurement region H. As the light-emitting unit E of the detection device 30C, a light-emitting element such as a light-emitting diode (LED) radiating incoherent light to the measurement region H is appropriately used. A VCSEL emitting a coherent laser beam may be used as the light-emitting unit E. The light-receiving unit R of the detection device 30C generates the detection signal ZC in accordance with a light reception level of light passing through the inside of the measurement region H like the light-receiving unit R of the detection device 30B. The detection signal ZC is a signal indicating a photoelectric volume pulse wave. A pressure sensor that generates a detection signal indicating displacement of the surface of the measurement region H (that is, indicating displacement of a blood vessel diameter) may be adopted as the detection device 30C.

The index calculation unit 51A according to the second embodiment calculates the blood mass index MA and the blood flow index FA of the measurement region H from the detection signal ZA generated by the detection device 30A as in the first embodiment. The index calculation unit 51A according to the second embodiment calculates the amplitude index using the blood mass index MA and the blood flow index FA generated by the index calculation unit 51A as in the first embodiment.

The index calculation unit 51B calculates a blood flow index FB from the detection signal ZB generated by the detection device 30B. The blood flow index FB is calculated in a scheme similar to the blood flow index FA (Expression (4a) or (4b)). The index calculation unit 51C calculates a blood mass index MC from the detection signal ZC generated by the detection device 30C. As described above, the blood mass index MA correlates with a blood vessel diameter. On the assumption of the foregoing relation, the index calculation unit 51C calculates displacement of a blood vessel diameter from the detection signal ZC and calculates the blood mass index MC from the displacement of the blood vessel diameter.

The amplitude calculation unit 531 according to the second embodiment calculates the amplitude index (ΔF/ΔM) of the blood mass index MA and the blood flow index FA calculated by the index calculation unit 51A as in the first embodiment. The resistance calculation unit 533 according to the second embodiment calculates the resistance index (SF/SM) from the blood flow index FB calculated by the index calculation unit 51B and the blood mass index MC calculated by the index calculation unit 51C. A method of calculating the resistance index is similar to that of the first embodiment. The pulse pressure calculation unit 535 calculates the pulse pressure ΔP in accordance with the amplitude index calculated by the amplitude calculation unit 531 and the resistance index calculated by the resistance calculation unit 533 as in the first embodiment. In the second embodiment, advantages similar to those of the first embodiment are obtained.

Third Embodiment

Figure 15:
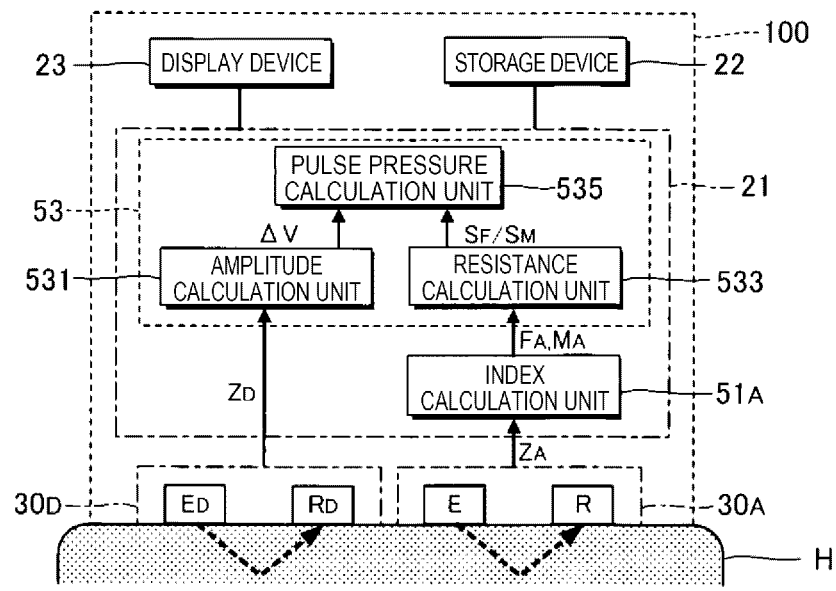
FIG. 15 is a diagram illustrating a configuration of a biological analysis device according to a third embodiment.

In the first embodiment, the ratio (ΔF/ΔM) correlating with the blood flow rate amplitude ΔV has been calculated as the amplitude index. In a third embodiment, however, the blood flow rate amplitude ΔV is calculated as the amplitude index. FIG. 15 is a diagram illustrating a configuration of a biological analysis device 100 according to the third embodiment. The biological analysis device 100 according to the third embodiment has a configuration in which a detection device 30D is added to the biological analysis device 100 of the first embodiment.

The detection device 30A according to the third embodiment has a configuration and a function similar to those of the first embodiment. The detection device 30D is an ultrasonic sensor module that generates the detection signal ZD in accordance with a state of the measurement region H. Specifically, the detection device 30D includes an emitting unit ED and a receiving unit RD. The emitting unit ED emits an ultrasonic wave to the measurement region H. On the other hand, the receiving unit RD generates a detection signal ZD in accordance with a reception level of the ultrasonic wave emitted from the emitting unit ED and passing through the inside of the measurement region H. For example, piezoelectric elements such as piezoelectric ceramics are used appropriately as the emitting unit ED and the receiving unit RD.

The index calculation unit 51A according to the third embodiment calculates the blood mass index MA and the blood flow index FA of the measurement region H from the detection signal ZA generated by the detection device 30A. The blood mass index MA and the blood flow index FA are calculated in methods similar to those of the first embodiment. The resistance calculation unit 533 according to the third embodiment calculates the resistance index using the blood mass index MA and the blood flow index FA generated by the index calculation unit 51A as in the first embodiment.

The amplitude calculation unit 531 according to the first embodiment has calculated the amplitude index from the blood mass index MA and the blood flow index FA calculated by the index calculation unit 51A. However, the amplitude calculation unit 531 according to the third embodiment directly calculates the amplitude index (the blood flow rate amplitude ΔV) from the detection signal ZD generated by the detection device 30D. The pulse pressure calculation unit 535 calculates the pulse pressure ΔP in accordance with the amplitude index (ΔV) calculated by the amplitude calculation unit 531 and the resistance index (SF/SM) calculated by the resistance calculation unit 533 as in the first embodiment.

In the third embodiment, advantages similar to those of the first embodiment are obtained. In the third embodiment, in particular, since the blood flow rate amplitude ΔV is calculated as the amplitude index, the pulse pressure ΔP can be calculated with higher precision than in the configuration in which the ratio (ΔF/ΔM) correlating with the blood flow rate amplitude ΔV is calculated as the amplitude index.

Fourth Embodiment

Figure 16:
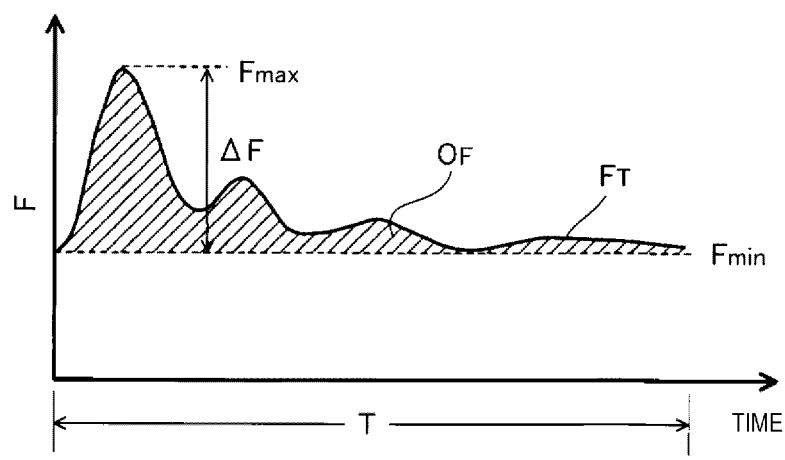
FIG. 16 is a graph illustrating a temporal change in a blood flow index.

FIG. 16 is a graph illustrating a temporal change FT in the blood flow index F. As exemplified in FIG. 16, an area OF of a region surrounded by a curve line indicating a temporal change FT in the blood flow index F and a straight line of a minimum value Fmin is equal to a product (ΔF× SF) of the amplitude ΔF and the blood flow integration value SF obtained by integrating the normalized blood flow indexes FN during the analysis period T. An area OM of a region surrounded by a curve line indicating the temporal change MT in the blood mass index M and a straight line of the minimum value Mmin is equal to a product (ΔM× SM) of the amplitude ΔM and the blood flow integration value SM obtained by integrating the normalized blood mass indexes MN during the analysis period T. Accordingly, Expression (5b) below is derived from Expression (5a) described above. As understood from Expression (5b), the pulse pressure ΔP is expressed as a product the coefficient K and a ratio of the area OF and the area OM (specifically, a ratio of the area OF to the area OM). For the foregoing reason, the pulse pressure ΔP is calculated from the area OF and the area OM according to the fourth embodiment.

$$\Delta P = K \times \frac{O_F}{O_M} \quad (5b)$$

Figure 17:
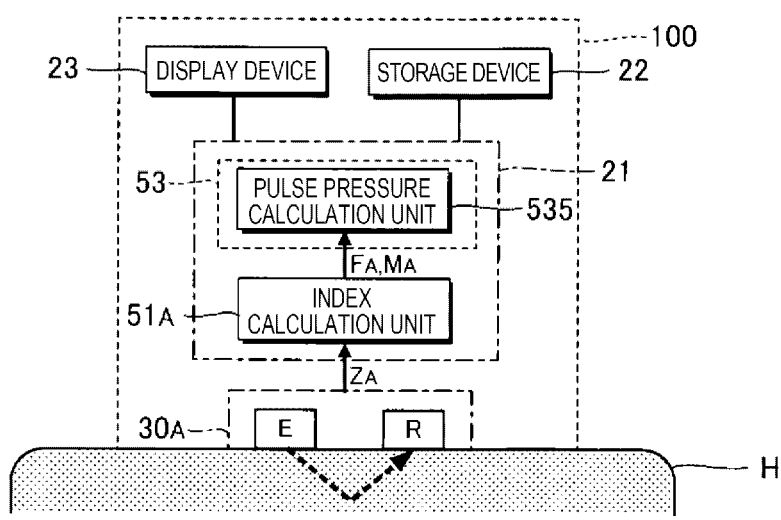
FIG. 17 is a diagram illustrating a configuration of a biological analysis device according to a fourth embodiment.

FIG. 17 is a diagram illustrating a configuration of a biological analysis device 100 according to a fourth embodiment. The biological analysis device 100 according to the fourth embodiment has a configuration in which the amplitude calculation unit 531 and the resistance calculation unit 533 are deleted from the control device 21 of the biological analysis device 100 of the first embodiment. The other remaining configuration is the same as that of the first embodiment.

The pulse pressure calculation unit 535 according to the fourth embodiment calculates the pulse pressure DP from the blood mass index MA and the blood flow index FA calculated by the index calculation unit 51A. The pulse pressure DP is calculated in accordance with the blood mass integration value SM obtained by integrating the blood mass indexes MA during the analysis period T and the blood flow integration value SF obtained by integrating the blood flow indexes FA during the analysis period T. In the fourth embodiment, the pulse pressure calculation unit 535 calculates the area OM as the blood mass integration value SM and calculates the area OF as the blood flow integration value SF. That is, in the fourth embodiment, the process (step Sa3) of calculating the amplitude index in FIG. 12 and the process (step Sa4) of calculating the resistance index are omitted. Specifically, the pulse pressure calculation unit 535 calculates the area OM and the area OF and calculates the pulse pressure DP by multiplying the ratio (OF/OM) of the area OF and the area OM by the coefficient K. The area OM is equivalent to the blood mass integration value SM obtained by integrating the blood mass indexes MA during the analysis period T and the area OF is equivalent to the blood flow integration value SF obtained by integrating the blood flow indexes FA during the analysis period T.

In the fourth embodiment, the advantage that the pulse pressure ΔP is calculated and a cuff is unnecessary in principle is realized as in the first embodiment. Accordingly, it is possible to reduce a physical load of the subject and calculate the pulse pressure ΔP with high precision. In the fourth embodiment, since it is unnecessary to calculate the amplitude ΔF and the amplitude ΔM and normalize the blood flow index F and the blood mass index M, a processing load for calculating the pulse pressure ΔP is reduced.

Fifth Embodiment

Figure 18:
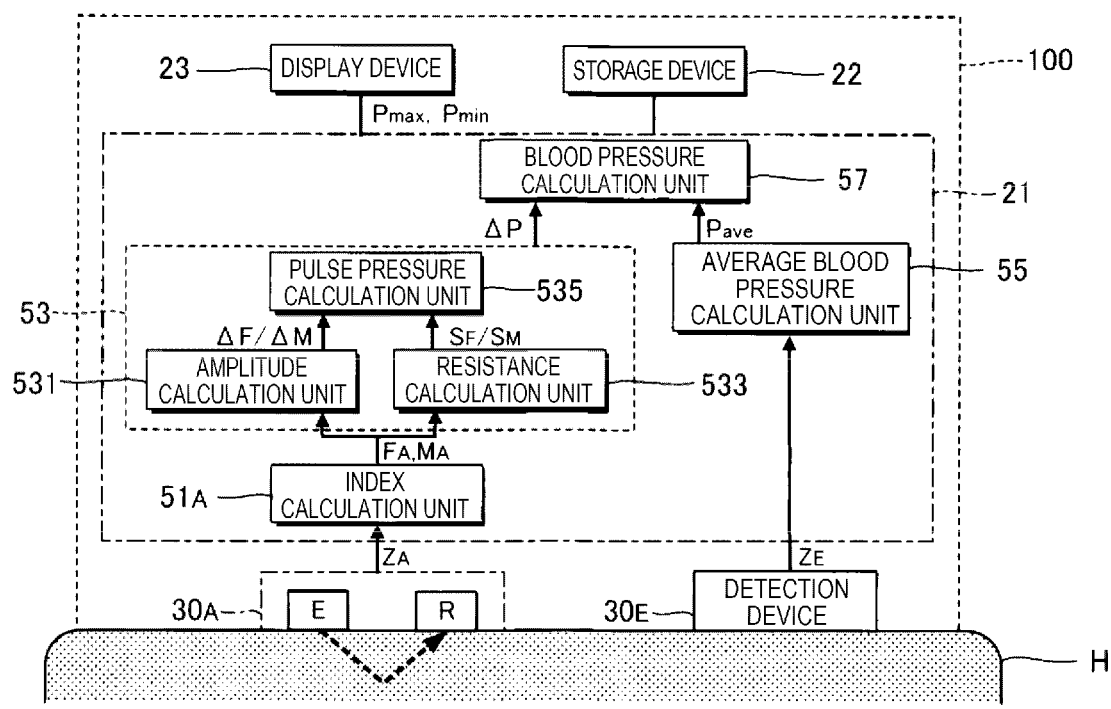
FIG. 18 is a diagram illustrating a configuration of a biological analysis device according to a fifth embodiment.

In a fifth embodiment, a configuration in which a blood pressure is calculated using the pulse pressure ΔP calculated in the first embodiment will be exemplified. FIG. 18 is a diagram illustrating a configuration of a biological analysis device 100 according to the fifth embodiment. The biological analysis device 100 according to the fifth embodiment has a configuration in which a detection device 30E, an average blood pressure calculation unit 55, a blood pressure calculation unit 57 are added to the biological analysis device 100 according to the first embodiment. The average blood pressure calculation unit 55 and the blood pressure calculation unit 57 are realized when the control device 21 executes a program stored in the storage device 22.

The detection device 30E is a detection device that generates a detection signal ZE in accordance with a state of the measurement region H (specifically, a blood vessel inside the measurement region H). For example, a device such as an optical sensor module or an ultrasonic sensor module is appropriately used as the detection device 30E. The average blood pressure calculation unit 55 calculates an average blood pressure Pave from the detection signal ZE generated by the detection device 30E. The average blood pressure Pave during the analysis period T exemplified in FIG. 2 is calculated. In the calculation of the average blood pressure Pave, any known technology can be adopted. The blood vessel calculation unit 53 calculates the pulse pressure ΔP as in the first embodiment.

The blood pressure calculation unit 57 in FIG. 18 calculates the blood pressure P from the pulse pressure ΔP calculated by the blood vessel calculation unit 53 and the average blood pressure Pave calculated by the average blood pressure calculation unit 55. The blood pressure calculation unit 57 according to the fifth embodiment calculates a systolic blood pressure Pmax and a diastolic blood pressure Pmin. As exemplified in FIG. 2, the systolic blood pressure Pmax is a maximum blood pressure during the analysis period T and the diastolic blood pressure Pmin is a minimum blood pressure during the analysis period T. Relations of Expressions (6) and (7) below are approximately established among the average blood pressure Pave, the pulse pressure ΔP, the systolic blood pressure Pmax, and the diastolic blood pressure Pmin. The blood pressure calculation unit 57 calculates the systolic blood pressure Pmax by Expression (6) below and calculates the diastolic blood pressure Pmin by Expression (7) below. The control device 21 causes the display device 23 to display the systolic blood pressure Pmax and a diastolic blood pressure Pmin calculated by the blood pressure calculation unit 57.

$$P_{max} = P_{ave} + \frac{2}{3}\Delta P \quad (6)$$

$$P_{min} = P_{ave} - \frac{1}{3}\Delta P \quad (7)$$

In the fifth embodiment, advantages similar to those of the first embodiment are obtained. In the fifth embodiment, in particular, since the blood pressures (the systolic blood pressure Pmax and a diastolic blood pressure Pmin) are calculated from the pulse pressure ΔP and the average blood pressure Pave, a cuff is unnecessary in principle in the calculation of a blood pressure.

Sixth Embodiment

Figure 19:
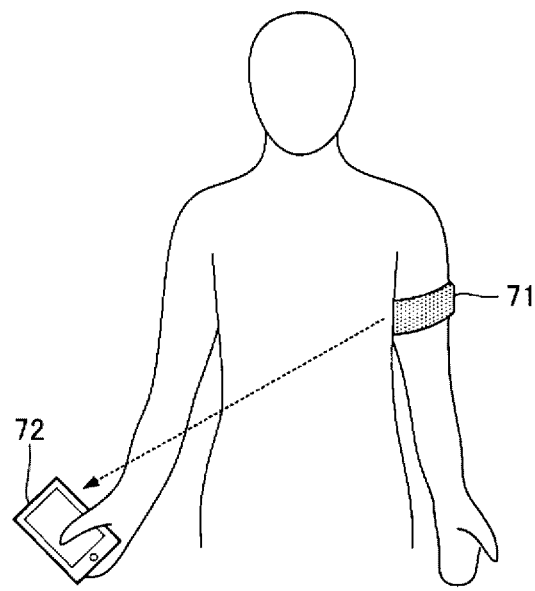
FIG. 19 is a schematic diagram illustrating a use example of a biological analysis device according to a sixth embodiment.
Figure 20:
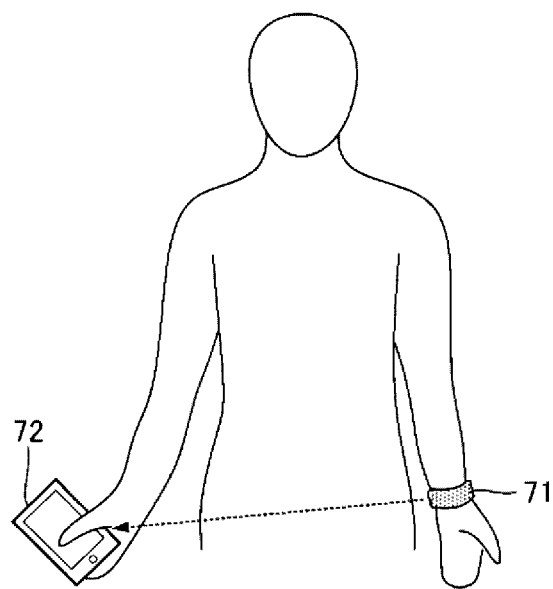
FIG. 20 is a schematic diagram illustrating another use example of a biological analysis device according to a sixth embodiment.

FIG. 19 is a schematic diagram illustrating a use example of a biological analysis device 100 according to a sixth embodiment. As exemplified in FIG. 19, the biological analysis device 100 includes a detection unit 71 and a display unit 72 configured to be separate from each other. The detection unit 71 includes detection device 30 exemplified each of the above-described embodiments. FIG. 19 exemplifies the detection unit 71 worn on an upper arm of a subject. As exemplified in FIG. 20, the detection unit 71 worn on a wrist of the subject is also appropriate.

The display unit 72 includes the display device 23 exemplified in each of the above-described embodiments. For example, an information terminal such as a mobile phone or a smartphone is an appropriate example of the display unit 72. Here, any specific form of the display unit 72 is used. For example, a wrist watch type information terminal which can be carried by the subject or an information terminal dedicated for the biological analysis device 100 may be used as the display unit 72.

An element (hereinafter referred to as a "calculation processing unit") calculating the pulse pressure ΔP from the detection signal Z is mounted on the display unit 72, for example. The calculation processing unit includes the elements exemplified in FIG. 3 (the index calculation unit 51 and the blood vessel calculation unit 53). The detection signals Z generated by the detection device 30 of the detection unit 71 are transmitted to the display unit 72 in a wired or wireless manner. The calculation processing unit of the display unit 72 calculates the pulse pressure ΔP from the detection signal Z and displays the pulse pressure ΔP on the display device 23. The average blood pressure calculation unit 55 and the blood pressure calculation unit 57 exemplified in the fifth embodiment can also be mounted on the display unit 72.

The calculation processing unit may be mounted on the detection unit 71. The calculation processing unit calculates the pulse pressure ΔP from the detection signal Z generated by the detection device 30 and transmits data for displaying the pulse pressure ΔP to the display unit 72 in a wired or wireless manner. The display device 23 of the display unit 72 displays the pulse pressure ΔP indicated by the data received from the detection unit 71. The calculation processing unit may transmit data for displaying the blood pressure calculated in the fifth embodiment to the display unit 72.

Seventh Embodiment

Noise distributed with a substantially equal intensity in a whole region on the frequency axis (hereinafter referred to as "background noise") can be contained in the intensity spectrum related to a frequency of the detection signal ZA. The background noise is shot noise unique to an electric circuit included in the biological analysis device 100 or noise caused due to an electromagnetic wave in an installation environment of the biological analysis device 100. In a seventh embodiment, the background noise is reduced from an intensity spectrum specified from the detection signal ZA, and the blood mass index M and the blood flow index F are calculated.

The detection device 30A according to the seventh embodiment generates a signal indicating the background noise (hereinafter referred to as an "observation signal") in addition to the detection signal ZA exemplified in each of the above-described embodiments. The observation signal is generated in a state in which a blood flow is not observed. For example, a signal output by the light-receiving unit R is generated as an observation signal in a state in which the light-emitting unit E radiates light to a stationary object with low reflectance without including a moving object. A signal output by the light-receiving unit R may be used as an observation signal in a state in which light is not radiated to a stationary object. A signal output by the light-receiving unit R may be used as an observation signal in a state in which the measurement region H or a position upstream from the measurement region H is stopped from bleeding by a cuff or the like. As understood from the foregoing description, an observation signal containing no component originating from a blood flow of the measurement region H is generated. That is, an observation signal indicating the background noise in a case in which the blood mass index M and the blood flow index F of the measurement region H are calculated is generated.

The index calculation unit 51A according to the seventh embodiment subtracts an intensity G(f)bg of the background noise from an intensity G(f) at each frequency f in an intensity spectrum related to the frequency of the detection signal ZA and calculates the blood mass index M and the blood flow index F. The intensity G(f)bg of the background noise is an intensity at each frequency f in the intensity spectrum calculated from the observation signal. A value obtained by smoothing the intensity G(f)bg of the background noise (for example, moving average) may be subtracted from the intensity G(f). The intensity G(f)bg may be smoothed on either the time axis or the frequency axis.

Specifically, the index calculation unit 51A specifies a correction intensity G(f)c by subtracting the intensity G(f)bg from the intensity G(f) at each frequency f. The correction intensity G(f)c is expressed in Expression (8) below.

$$G(f)c = G(f) - G(f)bg \quad (8)$$

The blood mass index M and the blood flow index F are calculated using the correction intensity G(f)c calculated from Expression (8). That is, the blood mass index M and the blood flow index F from which an influence of the background noise is reduced are calculated. As in each of the above-described embodiments, Expression (3a) or (3b) is used in the calculation of the blood mass index M, and Expression (4a) or (4b) is used in the calculation of the blood flow index F.

As understood from the foregoing description, according to the seventh embodiment, the intensity G(f)bg of the background noise is subtracted from the intensity G(f) at each frequency f in the intensity spectrum of the detection signal ZA to calculate the blood mass index M and the blood flow index F. Accordingly, the blood mass index M and the blood flow index F from which an influence of the background noise is reduced are calculated. That is, it is possible to calculate the pulse pressure ΔP with high precision.

As ascertained from Expression (4a) or (4b), the blood flow index F is calculated by multiplying the intensity G(f) by the frequency f (that is, using a frequency weighted intensity spectrum (f×G(f))). Accordingly, there is a tendency that the influence of the background noise increases with respect to the blood flow index F as the frequency f increases. The configuration in which the background noise is reduced from the intensity spectrum according to the seventh embodiment is particularly effective when the blood flow index F is calculated. The configuration of the seventh embodiment can be used to reduce the background noise from the intensity spectrum of the optically detected detection signal in the first to sixth embodiments.

Eighth Embodiment

When the background noise is removed at a frequency bandwidth (hereinafter referred to as a "designation bandwidth") in which the intensity G(f) is not changed in accordance with pulsation of the measurement region H in the intensity spectrum of the detection signal ZA, the intensity G(f) becomes closes to 0. As the intensity G(f) in the designation bandwidth is closer to 0, the background noise is paraphrased as being removed with high precision. Accordingly, in an eighth embodiment, the intensity G(f)bg is subtracted from the intensity G(f) so that a result obtained by subtracting the intensity G(f)bg from the intensity G(f) is closer to 0 in the designation bandwidth. The designation bandwidth is, for example, a bandwidth equal to or greater than 25 kHz or equal to or less than 30 kHz. The designation bandwidth is not limited to the foregoing example. For example, the designation bandwidth is changed appropriately in accordance with the kind of measurement region H.

The index calculation unit 51A according to the eighth embodiment calculates the blood mass index M and the blood flow index F by subtracting the intensity G(f)bg of the background noise from the intensity G(f) at each frequency f in the intensity spectrum related to the frequency of the detection signal ZA as in the seventh embodiment. Specifically, the index calculation unit 51A calculates the correction intensity G(f)c by subtracting the intensity G(f)bg from the intensity G(f) so that the result obtained by subtracting the intensity G(f)bg from the intensity G(f) is close to 0 in the designation bandwidth. The correction intensity G(f)c according to the eighth embodiment is expressed in Expression (9) below.

$$G(f)c = G(f) - C \times G(f)bg \tag{9}$$

A sign C in Expression (9) is a coefficient set so that the correction intensity G(f)c in the designation bandwidth is closer to 0. Specifically, the coefficient C is set so that a value calculated from Expression (10) below is minimum (ideally, 0). A sign fmax of Expression (9) is an upper limit of the frequency of the designation bandwidth and fmin is a lower limit of the frequency of the designation bandwidth. The coefficient C may be set in accordance with the frequency f. For example, the coefficient C different for each bandwidth segmented into a plurality of pieces on the frequency axis may be set.

$$\sum_{fmin}^{fmax} (G(f) - C \times G(f)bg)^2 \tag{10}$$

As ascertained from Expression (9), the correction intensity G(f)c is calculated by subtracting the intensity G(f)bg multiplied by the coefficient C from the intensity G(f). The index calculation unit 51A calculates the blood mass index M and the blood flow index F using the correction intensity G(f)c calculated by Expression (9) at each frequency f. As in each of the above-described embodiments, Expression (3a) or (3b) is used in the calculation of the blood mass index M, and Expression (4a) or (4b) is used in the calculation of the blood flow index F.

Figure 21:
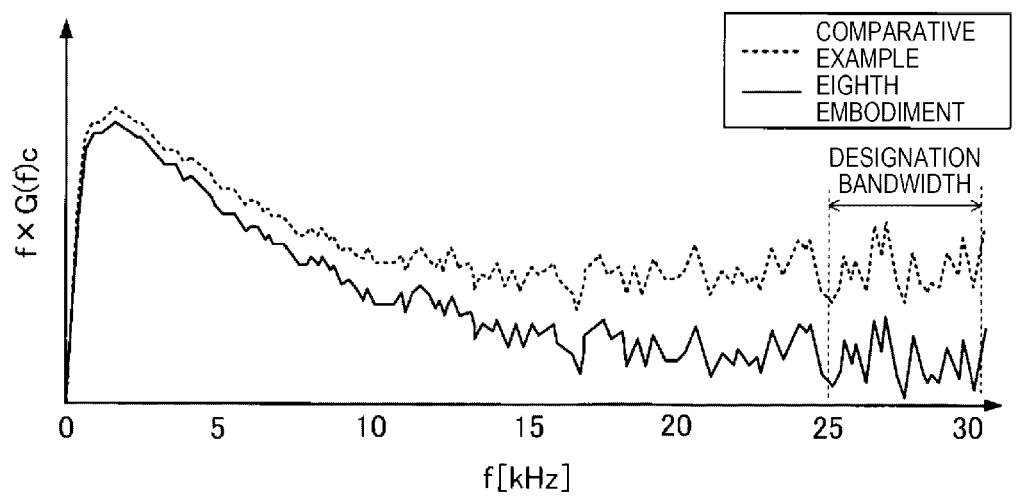
FIG. 21 is a graph illustrating a frequency weighted intensity spectrum according to each of an eighth embodiment and a comparative example.

FIG. 21 is graph illustrating the frequency weighted intensity spectrum (f×G(f)c) calculated in a configuration in which the correction intensity G(f)c is calculated without multiplying the intensity G(f)b by the coefficient C (hereinafter referred to as a "comparative example") and the frequency weighted intensity spectrum (f×G(f)c) calculated from the correction intensity G(f)c by calculating Expression (9). As ascertained from FIG. 21, in the configuration of the eighth embodiment, the frequency weighted intensity spectrum (f×G(f)c) in which the background noise is reduced with higher precision is calculated than in the comparative example. In particular, the background noise is effectively reduced on a high bandwidth in which an influence of the background noise increases and the frequency weighted intensity spectrum (f×G(f)c) is calculated. That is, it is possible to calculate the blood flow index F from which the background noise is effectively reduced over the whole frequency axis.

In the eighth embodiment, advantages similar to those of the first embodiment are obtained. In the eighth embodiment, the blood mass index M and the blood flow index F in which the influence of the background noise is reduced are calculated as in the seventh embodiment. According to the eighth embodiment, in particular, the blood mass index M and the blood flow index F are calculated by subtracting the intensity G(f)bg from the intensity G(f) so that the result obtained by subtracting the intensity G(f)bg from the intensity G(f) is closer to 0 in the designation bandwidth. Accordingly, it is possible to reduce the influence of the background noise with higher precision and calculate the blood mass index M and the blood flow index F than in the comparative example.

Examination on Presence or Absence of Each Configuration

As has been exemplified in each of the above-described embodiments, according to a preferred aspect of the invention, a configuration in which the pulse pressure ΔP is calculated in accordance with the blood mass integration value SM obtained by integrating the blood mass indexes M during an integration period and the blood flow integration value SF obtained by integrating the blood flow indexes F during the integration period (hereinafter referred to as a "configuration A") is adopted. A method of determining whether the configuration A is adopted in an actual biological analysis device (hereinafter referred to as an "actual product") 90 will be described below. Hereinafter, the biological analysis device 100 for which it is confirmed that the configuration A is adopted is referred to as a "product of the present specification".

Figure 22:
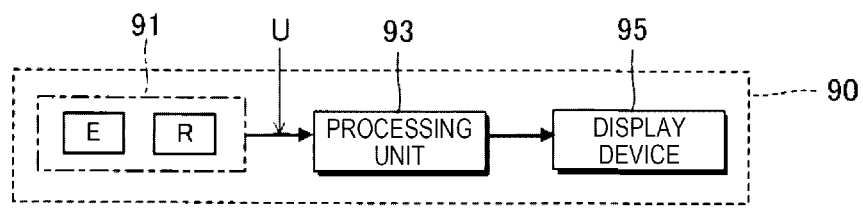
FIG. 22 is a diagram illustrating a configuration of an actual product.

The actual product 90 includes a detection device that includes the light-emitting unit E and the light-receiving unit R, a processing unit 93 that calculates a pulse pressure ΔPw from a detection signal output by the detection device 91, and a display device 95 that displays the pulse pressure ΔPw calculated by the processing unit 93, as exemplified din FIG. 22. A scene in which a plurality (for example, 3 or more kinds) of test signals U with different waveforms within the analysis period T are supplied in order to each of the processing unit 93 of the actual product 90 and the control device of the product of the present specification is assumed. In the actual product 90, each test signal U (U1, U2, and U3) is supplied to the processing unit 93 (for example, a wiring or a terminal between the detection device 91 and the processing unit 93). For example, each test signal U is generated by a signal generator such as a pulse generator. The plurality of test signals U have different products ((ΔF/ΔM)× (SF/SM)) of the amplitude indexes and the resistance indexes. For example, the plurality of test signals U are generated so that a difference between a maximum value and a minimum value among the products ((ΔF/ΔM)× (SF/SM)) calculated in the plurality of test signals U is twice or more. The test signals U with wavelengths of a time length longer than the analysis period T may be generated.

A case in which the pulse pressure ΔPw of a subject is displayed as a measurement result on the display device 95 of the actual product 90 is assumed. It is assumed that a pulse pressure ΔPw1 is displayed when the test signal U1 is supplied to the actual product 90, a pulse pressure ΔPw2 is displayed when the test signal U2 is supplied to the actual product 90, and a pulse pressure ΔPw3 is displayed when the test signal U3 is supplied to the actual product 90. It is assumed that the pulse pressure ΔP1 is displayed when the test signal U1 is supplied to the product of the present specification, the pulse pressure ΔP2 is displayed when the test signal U2 is supplied to the product of the present specification, and the pulse pressure ΔP3 is displayed when the test signal U3 is supplied to the product of the present specification.

Figure 23:
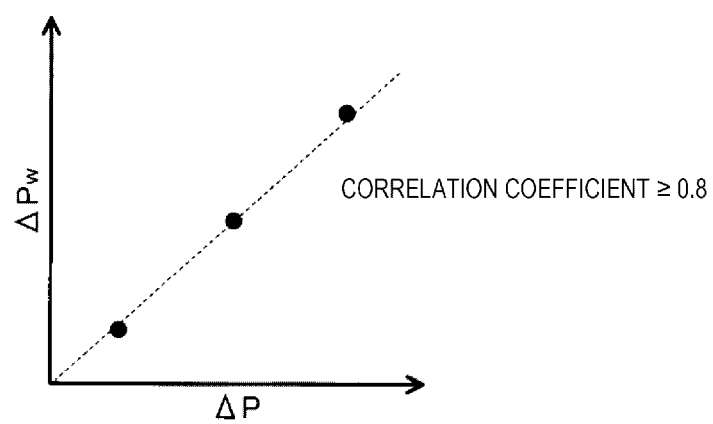
FIG. 23 is a graph illustrating a relation between a pulse pressure displayed for an actual product and a pulse pressure displayed for a product of the present specification.

FIG. 23 is a graph illustrating a relation between the pulse pressure ΔPw displayed on the actual product 90 and the pulse pressure ΔP displayed on the product of the present specification. When the configuration A is adopted in the actual product 90, correlation is observed between the plurality of pulse pressures ΔPw (ΔPw1, ΔPw2, and ΔPw3) measured with the actual product 90 and the plurality of pulse pressures ΔP (ΔP1, ΔP2, and ΔP3) measured with the product of the present specification. Specifically, a correlation coefficient between the plurality of pulse pressures ΔPw displayed on the actual product 90 and the plurality of pulse pressures ΔP displayed with the product of the present specification is 0.8 or more. In consideration of the foregoing circumstances, there is a sufficiently high possibility of the configuration A being adopted in the actual product 90 when the correlation coefficient between the pulse pressures ΔPw calculated by supplying the plurality of test signals U to the actual product 90 and the pulse pressures ΔP calculated by supplying the plurality of test signals U to the product of the present specification is 0.8 or more. For example, a Pearson integration correlation coefficient is suitable as the correlation coefficient.

In the foregoing description, the test signals U have been supplied to the processing unit 93 of the actual product 90, but the pulse pressures ΔPw calculated by causing the light-receiving unit R that generates a detection signal in the actual product 90 to receive light by which the test signals U are generated may be compared with the pulse pressures ΔP of the product of the present specification. In the foregoing description, the pulse pressures ΔPw displayed on the display device 95 of the actual product 90 have been compared with the pulse pressures ΔP displayed on the display device of the product of the present specification, but whether the actual product 90 has the configuration A may be determined by comparing data output from the processing unit 93 of the actual product 90 with data output from the control device of the product of the present specification.

In the foregoing description, the case in which the actual product 90 displays the pulse pressures ΔPw has been assumed for convenience, but whether the actual product 90 has the configuration A can be estimated in accordance with a similar method even when the actual product 90 displays the blood pressures P (the systolic blood pressure Pmax and the diastolic blood pressure Pmin) of a subject. That is, a correlation coefficient is calculated between the plurality of blood pressures P measured by sequentially supplying the plurality of test signals U to the actual product 90 and the plurality of blood pressures P measured by sequentially supplying the plurality of test signals U to the product of the present specification (in the fifth embodiment). When the correlation coefficient is 0.8 or more, there is a high possibility of the configuration A being adopted in the actual product 90.

When the actual product 90 outputs the resistance index of a subject, whether the actual product 90 has a configuration in which the ratio of the blood mass integration value SM and the blood flow integration value SF is calculated as the resistance index (hereinafter referred to as a "configuration B") can be estimated in accordance with a method similar to the above-described method. Specifically, a correlation coefficient is calculated between the plurality of ratios (SF/SM) calculated by supplying the actual product 90 with the plurality of test signals U with different ratios (SF/SM) of the blood mass integration value SM and the blood flow integration value SF and the plurality of ratios (SF/SM) estimated by sequentially supplying the product of the present specification with the plurality of test signals U. There is a high possibility of the configuration B being adopted in the actual product 90 when the correlation coefficient is 0.8 or more.

When the actual product 90 outputs the amplitude index of a subject, whether the actual product 90 has a configuration in which the ratio of the amplitude ΔM and the amplitude ΔF is calculated as the amplitude index (hereinafter referred to as a "configuration C") can be estimated in accordance with a method similar to the above-described method. Specifically, a correlation coefficient is calculated between the plurality of ratios (ΔF/ΔM) calculated by supplying the actual product 90 with the plurality of test signals U with different ratios (ΔF/ΔM) of the amplitude ΔM and the amplitude ΔF and the plurality of ratios (ΔF/ΔM) calculated by sequentially supplying the product of the present specification with the plurality of test signals U. There is a high possibility of the configuration C being adopted in the actual product 90 when the correlation coefficient is 0.8 or more.

As described above, according to the configuration C, the advantage that the amplitude index can be calculated with high precision is realized even when a skin thickness is changed. Accordingly, whether the actual product 90 has the configuration C is estimated in accordance with the following method. First, the amplitude indexes are calculated in the actual product 90 and the product of the present specification in a plurality of cases in which a human model in which a pseudo-blood vessel in which blood flows is assumed and a skin thickness of the human model is changed. When a correlation coefficient between the plurality of amplitude indexes calculated in the actual product 90 and the plurality of amplitude indexes calculated in the product of the present specification is 0.8 or more, there is a high possibility of the configuration C being adopted in the actual product 90. The amplitude indexes are calculated in the actual product 90 and the product of the present specification in a plurality of cases in which a distance between the light-emitting unit E and the light-receiving unit R is changed in each of the actual product 90 and the product of the present specification. When a correlation coefficient between the plurality of amplitude indexes calculated in the actual product 90 and the plurality of amplitude indexes calculated in the product of the present specification is 0.8 or more, there is a high possibility of the configuration C being adopted in the actual product 90.

In the seventh and eighth embodiments, a configuration in which the blood mass index M and the blood flow index F are calculated by subtracting the intensity G(f)bg of the background noise from the intensity G(f) at each frequency f in the intensity spectrum related to the frequency of the detection signal ZA (hereinafter referred to as a "configuration D") is adopted. A method of determining whether the configuration D is adopted in the actual product 90 will be described below.

In a state in which the measurement region H or a position upstream from the measurement region H is stopped from bleeding (hereinafter referred to as a "bleeding stop state"), the pulse pressure ΔP is calculated by the actual product 90. In the intensity spectrum specified by the actual product 90 in the bleeding stop state, the background noise is predominantly contained. When the configuration D is adopted in the actual product 90, the pulse pressure ΔP is a value close to 0 (ideally, 0) in the bleeding stop state. On the other hand, when the configuration D is adopted in the actual product 90, the pulse product ΔP is a value deviating from 0 due to an influence of the background noise contained in the intensity spectrum. As understood from the foregoing description, there is a high possibility of the configuration D being adopted when the pulse pressure ΔP displayed on the actual product 90 is close to 0 in the bleeding stop state. When the actual product 90 displays the blood mass index M or the blood flow index F, whether the configuration D is adopted may be determined by determining whether the blood mass index M or the blood flow index F calculated in the bleeding stop state is close to 0.

Modification Examples

Each of the embodiments exemplified above can be modified in various forms. Specific modification aspects will be exemplified below. Two or more selected arbitrarily from the following examples can also be merged appropriately.

Figure 24:
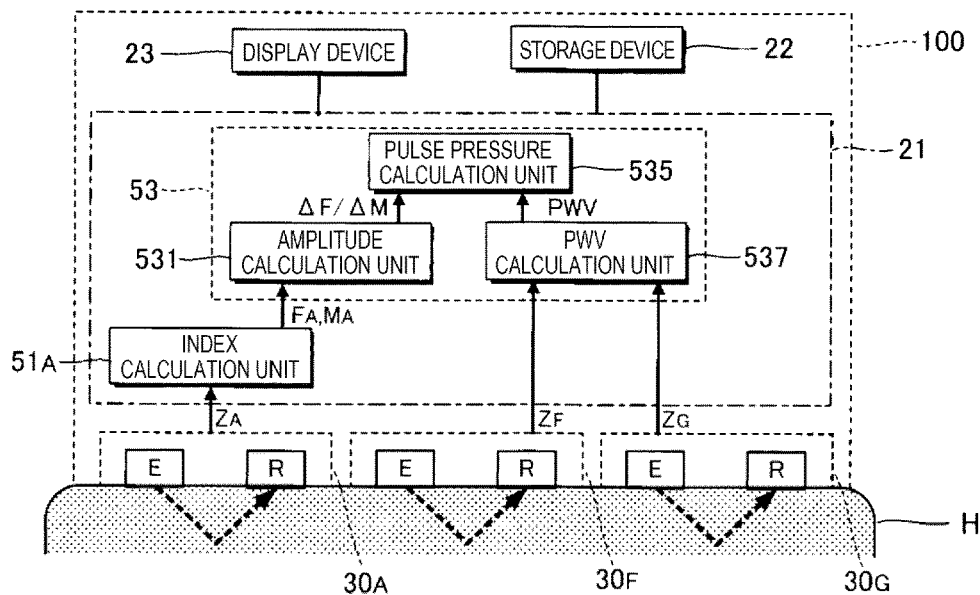
FIG. 24 is a diagram illustrating a configuration of a biological analysis device according to a modification example.

(1) In the first embodiment, the ratio (SF/SM) of the blood mass integration value SM and the blood flow integration value SF has been calculated as the resistance index, but the resistance index is not limited to the foregoing example. For example, the pulse wave velocity PWV can also be calculated as the resistance index. FIG. 24 is a diagram illustrating a configuration of the biological analysis device 100 according to a modification example. The biological analysis device 100 according to the modification example has a configuration in which two detection devices 30 (30F and 30G) are added to the biological analysis device 100 of the first embodiment and a PWV calculation unit 537 is included instead of the resistance calculation unit 533 of the first embodiment. Each detection device 30 (30F and 30G) is, for example, an optical sensor module similar to the detection device 30A and generates the detection signal Z in which a state of the measurement region H is reflected. The PWV calculation unit 537 calculates a pulse wave velocity PWV as the resistance index using a detection signal ZF generated by the detection device 30F and a detection signal ZG generated by the detection device 30G. The pulse pressure calculation unit 535 calculates the pulse pressures ΔP in accordance with the amplitude index calculated by the amplitude calculation unit 531 and the resistance index calculated by the PWV calculation unit 537. The foregoing modification example can also be applied to the second, third, and fifth embodiments.

(2) In each of the above-described embodiments, the blood vessel calculation unit 53 has calculated the pulse pressures ΔP, but the index calculated by the blood vessel calculation unit 53 is not limited to the pulse pressure ΔP. For example, the blood vessel calculation unit 53 may specify an index (for example, abnormality/high side/normality or the like) indicating a state of the pulse pressures ΔP of a subject using the calculated pulse pressures ΔP. As understood from the foregoing description, the index calculated by the blood vessel calculation unit 53 is expressed comprehensively as an index related to the pulse pressure ΔP (hereinafter referred to as a "pulse pressure index") and the pulse pressure index includes both the pulse pressure ΔP and an index calculated using the pulse pressure ΔP.

The blood vessel calculation unit 53 may calculate an index other than the pulse pressure index. Here, there is a tendency that blood vessel resistance increases when arteriosclerosis progresses. As described above, since the resistance index correlates with blood vessel resistance, the resistance index can be used as an arteriosclerosis index. Accordingly, the resistance index calculated by the blood vessel calculation unit 53 may be presented to a user. Specifically, a blood vessel resistance unit calculates a resistance index in accordance with the blood mass integration value SM and the blood flow integration value SF (calculates the ratio (SF/SM) as the resistance index) and causes the display device 23 to display the resistance index. The blood vessel calculation unit 53 may calculate the ratio (SF/SM) and calculate the pulse wave velocity PWV from the ratio (SF/SM) as the resistance index. The blood vessel calculation unit may calculate an index indicating the degree of arteriosclerosis from the calculated ratio (SF/SM) or the pulse wave velocity PWV as the resistance index. That is, the resistance index is expressed comprehensively as, for example, an index related to the blood vessel resistance of a biological body. As understood from the foregoing description, the index calculated by the blood vessel calculation unit 53 is expressed comprehensively as an index related to a blood vessel (hereinafter referred to as a "blood vessel index") and, the blood vessel index includes both the pulse pressure index and the resistance index. That is, the blood vessel calculation unit 53 functions as an element that calculates a blood vessel index in accordance with the blood mass integration value SM and the blood flow integration value SF (generally, in accordance with the ratio of the blood mass integration value SM and the blood flow integration value SF).

The blood vessel calculation unit 53 may calculate an amplitude index and cause the display device 23 to display the amplitude index. As understood from the above description, the amplitude index and the resistance index calculated by the blood vessel calculation unit 53 may be presented as independent indexes to a subject. Even in the configuration in which the amplitude index or the resistance index is calculated as an independent index, a cuff is not necessary in principle. Thus, it is possible to calculate each index with high precision while reducing a physical load on the subject.

(3) In the first embodiment, the ratio (SF/SM) of the blood mass integration value SM and the blood flow integration value SF has been calculated as the resistance index, but a value calculated as the resistance index is not limited to the ratio (SF/SM). For example, a configuration in which the resistance index is calculated by substituting the ratio (SF/SM) to a predetermined function or a configuration in which the resistance index is calculated by multiplying the ratio (SF/SM) by a coefficient can also be adopted. For example, a configuration in which a difference between the blood mass integration value SM and the blood flow integration value SF is calculated as the resistance index can also be adopted. However, in the configuration in which the resistance index is calculated using the ratio of the blood mass integration value SM and the blood flow integration value SF, the resistance index can be calculated with high precision using the tendency that the ratio of the blood mass integration value SM and the blood flow integration value SF correlates with the pulse wave velocity. The foregoing modification example can also be applied to the second, third, and fifth embodiments.

(4) In the first embodiment, the ratio ($\Delta F/\Delta M$) of the amplitude $\Delta F$ and the amplitude $\Delta M$ has been calculated as the amplitude index, but a value calculated as the amplitude index is not limited to the ratio ($\Delta F/\Delta M$). For example, a configuration in which the ratio ($\Delta F/\Delta M$) is substituted to a predetermined function or a configuration in which the amplitude index is calculated by multiplying the ratio ($\Delta F/\Delta M$) by a coefficient can also be adopted. For example, a configuration in which a difference between the amplitude $\Delta F$ and the amplitude $\Delta M$ is calculated as the amplitude index can also be adopted. Here, in the configuration in which the amplitude index is calculated using the ratio of the amplitude $\Delta F$ and the amplitude $\Delta M$, the amplitude index can be calculated with high precision using the tendency that the ratio ($\Delta F/\Delta M$) of the amplitude $\Delta M$ and the amplitude $\Delta F$ correlates to the blood flow rate. It is possible to calculate the amplitude index while reducing an influence of a skin thickness.

(5) In each of the above-described embodiments, the temporal change MT in the blood mass index M during one analysis period T has been used in the calculation of the pulse pressure $\Delta P$, but the temporal change MT obtained by averaging the temporal changes MT in the blood mass index M in each of the plurality of analysis periods T over the plurality of analysis periods T may be used in the calculation of the pulse pressure $\Delta P$. For the blood flow index F, the temporal change FT obtained by averaging the temporal changes FT in the blood flow index F in each of the plurality of analysis periods T over the plurality of analysis periods T may be used in the calculation of the pulse pressure $\Delta P$.

(6) In the first embodiment, each of the blood mass index MA and the blood flow index FA has been normalized within the normalization range equal to or greater than 0 and equal to or less than 1, but any upper limit and any lower limit of the normalization range can be used as long as the blood mass index MA and the blood flow index FA are normalized in a common range. The foregoing modification example can also be applied to the second, third, and fifth embodiments.

(7) In each of the above-described embodiments, the biological analysis device 100 configured as a single device has been exemplified, but the plurality of components of the biological analysis device 100 can be realized as mutually separate devices, as will be exemplified below. In the following description, an element calculating the pulse pressure $\Delta P$ from the detection signal ZA is referred to as a "calculation processing unit 27". The calculation processing unit 27 includes, for example, the components exemplified in FIG. 3 (the index calculation unit 51 and the blood vessel calculation unit 53).

Figure 25:
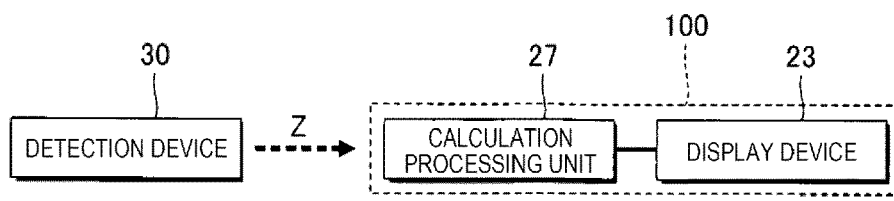
FIG. 25 is a diagram illustrating a configuration of a biological analysis device according to a modification example.

In each of the above-described embodiments, the biological analysis device 100 including the detection devices 30 (30A, 30B, 30C, 30D, and 30E) has been exemplified, but as exemplified in FIG. 25, the detection device 30 is assumed to be separate from the biological analysis device 100. The detection device 30 is, for example, a portable optical sensor module that is worn on the measurement region H such as a wrist, an upper wrist, or the like of a subject. The biological analysis device 100 is realized as, for example, an information terminal such as a mobile phone or a smartphone. The biological analysis device 100 may be realized as a wrist watch type information terminal. The detection signal Z generated by the detection device 30 is transmitted to the biological analysis device 100 in a wired or wireless manner. The calculation processing unit 27 of the biological analysis device 100 calculates the pulse pressure $\Delta P$ from the detection signal Z and displays the pulse pressure $\Delta P$ on the display device 23. As understood from the foregoing description, the detection device 30 can be omitted from the biological analysis device 100.

Figure 26:
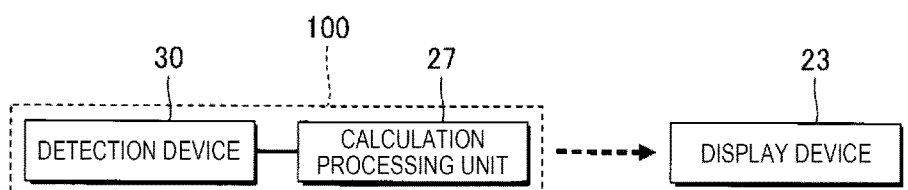
FIG. 26 is a diagram illustrating a configuration of a biological analysis device according to a modification example.

In each of the above-described embodiments, the biological analysis device 100 including the display device 23 has been exemplified, but as exemplified in FIG. 26, the display device 23 may be configured to be separate from the biological analysis device 100. The calculation processing unit 27 of the biological analysis device 100 calculates the pulse pressure $\Delta P$ from the detection signal Z and transmits data for displaying the pulse pressure $\Delta P$ to the display device 23. The display device 23 may be a dedicated display device, but may be mounted on, for example, an information terminal such as a mobile phone or a smartphone or a wrist watch type information terminal which can be carried by a subject. The pulse pressure $\Delta P$ calculated by the calculation processing unit 27 of the biological analysis device 100 are transmitted to the display device 23 in a wired or wireless manner. The display device 23 displays the pulse pressure $\Delta P$ received from the biological analysis device 100. As understood from the foregoing description, the display device 23 can be omitted from the biological analysis device 100.

Figure 27:
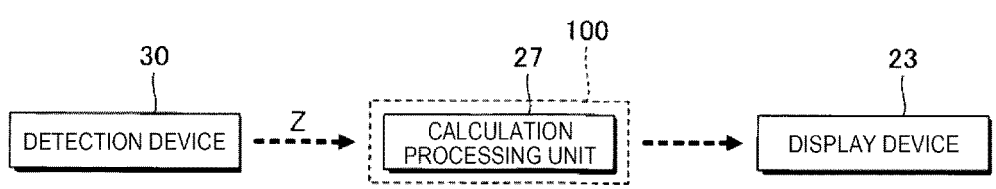
FIG. 27 is a diagram illustrating a configuration of a biological analysis device according to a modification example.

As exemplified in FIG. 27, the detection device 30 and the display device 23 are assumed to be separate from the biological analysis device 100 (the calculation processing unit 27). For example, the biological analysis device 100 (the calculation processing unit 27) is mounted on an information terminal such as a mobile phone or a smartphone.

In the configuration in which the detection device 30 is separate from the biological analysis device 100, the index calculation unit 51 can also be mounted on the detection device 30. The blood mass index M and the blood flow index F calculated by the index calculation unit 51 are transmitted from the detection device 30A to the biological analysis device 100 in a wired or wireless manner. As understood from the foregoing description, the index calculation unit 51 can be omitted from the biological analysis device 100.

(8) In each of the above-described embodiments, the wrist watch type biological analysis device 100 including the casing 12 and the belt 14 has been exemplified, but any specific form of the biological analysis device 100 can be used. For example, the biological analysis device 100 of any type such as a patch type which can be attached to the body of a subject, an ear-mounted type which can be mounted on the ears of a subject, a finger-mounted type (for example, a nail-mounted type) which can be mounted on a finger of a subject), or a head-mounted type which can be mounted on the head of a subject can be adopted.

(9) In each of the above-described embodiments, the pulse pressure ΔP of a subject has been displayed on the display device 23, but the configuration in which the subject is informed of the pulse pressure ΔP is not limited to the foregoing example. For example, a subject can also be informed of the pulse pressure ΔP by sound. In the ear-mounted type biological analysis device 100 which can be mounted on the ears of a subject, a configuration in which the subject is informed of the pulse pressure ΔP by sound is particularly appropriate. The subject may not necessarily be informed of the pulse pressure ΔP. For example, the pulse pressure ΔP calculated by the biological analysis device 100 may be transmitted from a communication network to another communication device. The pulse pressure ΔP may be stored in a portable recording medium detachably mounted on the storage device 22 of the biological analysis device 100 or the biological analysis device 100.

(10) The biological analysis device 100 according to each of the above-described embodiments is realized in cooperation with the control device 21 and a program, as exemplified above. The program according to a preferred aspect of the invention can be provided in a form stored a recording medium which can be read by the computer to be installed on the computer. The program stored in a recording medium included in a delivery server can also be provided to a computer in a form delivered via a communication network. The recording medium is, for example, a non-transitory recording medium. An optical recording medium (optical disc) such as a CD-ROM is a good example, but a recording medium with any known format such as a semiconductor recording medium or a magnetic recording medium can be included. The non-transitory recording medium includes any recording medium removing a transitory and propagating signal, and a volatile recording medium is not excluded.

The entire disclosures of Japanese Patent Application No. 2017-157160, filed Aug. 16, 2017 and Japanese Patent Application No. 2018-104932, filed May 31, 2018 are expressly incorporated by reference herein.

What is claimed is:

1. A biological analysis device comprising:
a controller configured to
receive a signal corresponding to blood mass indexes that indicate blood mass of a biological body flowing through a blood vessel,
receive a signal corresponding to blood flow indexes that indicate volume of blood flow of the biological body flowing through the blood vessel,
calculate a blood vessel index related to the blood vessel of the biological body by integrating the blood mass indexes during an integration period to obtain a blood mass integration value, by integrating the blood flow indexes during the integration period to obtain a blood flow integration value, and by calculating a ratio of the blood mass integration value and the blood flow integration value, and
output a signal corresponding to the blood vessel index; and
a display configured to receive the signal to present the blood vessel index.

2. The biological analysis device according to claim 1, wherein the controller is configured to calculate a pulse pressure index related to a pulse pressure.

3. The biological analysis device according to claim 2, wherein the controller is configured to
calculate a ratio of an amplitude of a temporal change in the blood mass index and an amplitude of a temporal change in the blood flow index as an amplitude index related to an amplitude of a temporal change in a blood flow rate of the biological body, and
calculate the pulse pressure index in accordance with the amplitude index and the blood vessel index.

4. The biological analysis device according to claim 1, wherein the controller is configured to calculate the blood mass integration value by integrating numerical values in which the blood mass indexes are normalized within a normalization range during the integration period and the blood flow integration value by integrating numerical values in which the blood flow indexes are normalized within the normalization range during the integration period.

5. The biological analysis device according to claim 1, wherein the blood vessel index is a resistance index related to blood vessel resistance of the biological body.

6. The biological analysis device according to claim 1, wherein the biological analysis device is configured to be mounted on an upper arm of a wrist of the biological body.

7. The biological analysis device according to claim 1, further comprising:
a light source that is configured to radiate a laser beam to the biological body;
a light sensor that is configured to receive the laser beam reflected inside the biological body; wherein the controller is configured to
calculate the blood mass indexes and the blood flow indexes using a detection signal indicating a light reception level by the light sensor.

8. The biological analysis device according to claim 7, wherein the controller is configured to calculate the blood mass indexes by integrating an intensity of each frequency in an intensity spectrum related to a frequency of the detection signal in a predetermined frequency range.

9. The biological analysis device according to claim 7, wherein the controller is configured to calculate the blood flow indexes by integrating products of the intensity of each frequency and the frequency in an intensity spectrum related to a frequency of the detection signal within a predetermined frequency range.

10. A biological analysis method comprising:
receiving a signal corresponding to blood mass indexes that indicate blood mass of a biological body flowing through a blood vessel;
receiving a signal corresponding to blood flow indexes that indicate volume of blood flow of the biological body flowing through the blood vessel;

calculating a blood vessel index related to the blood vessel of the biological body by (a) integrating the blood mass indexes during an integration period to obtain a blood mass integration value, (b) integrating the blood flow indexes during the integration period to obtain a blood flow integration value, and (c) calculating a ratio of the blood mass integration value and the blood flow integration value;

generating a signal corresponding to the blood vessel index; and displaying the blood vessel index on a display using the signal.

11. A non-transitory computer readable medium storing a program that causes a computer to:

receive a signal corresponding to blood mass indexes that indicate blood mass of a biological body flowing through a blood vessel;

receive a signal corresponding to blood flow indexes that indicate volume of blood flow of the biological body flowing through the blood vessel;

calculate a blood vessel index related to the blood vessel of the biological body by (a) integrating the blood mass indexes during an integration period to obtain a blood mass integration value, (b) integrating the blood flow indexes during the integration period to obtain a blood flow integration value, and (c) calculating a ratio of the blood mass integration value and the blood flow integration value;

generate a signal corresponding to the blood vessel index; and display the blood vessel index on a display using the signal.

* * * * *